US008263624B2

(12) United States Patent
Härter et al.

(10) Patent No.: US 8,263,624 B2
(45) Date of Patent: Sep. 11, 2012

(54) ARYL-SUBSTITUTED HETEROCYCLES, AND USE THEREOF

(75) Inventors: Michael Härter, Leverkusen (DE); Tobias Wunberg, Österreich (AT); Swen Allerheiligen, Essen (DE); Marcus Bauser, Wuppertal (DE); Ulrich Rester, Wuppertal (DE); Stefan Heitmeier, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 667 days.

(21) Appl. No.: 12/302,503

(22) PCT Filed: May 25, 2007

(86) PCT No.: PCT/EP2007/004693
§ 371 (c)(1),
(2), (4) Date: Aug. 28, 2009

(87) PCT Pub. No.: WO2007/127791
PCT Pub. Date: Dec. 6, 2007

(65) Prior Publication Data
US 2010/0029651 A1 Feb. 4, 2010

(30) Foreign Application Priority Data

May 31, 2006 (DE) .......................... 10 2006 025 314

(51) Int. Cl.
*A61K 31/44* (2006.01)
*A61K 31/422* (2006.01)
*A61K 31/4523* (2006.01)
*A61K 31/4164* (2006.01)
*A61K 31/506* (2006.01)
*A61K 31/5377* (2006.01)
*A61K 31/5355* (2006.01)
*C07D 231/12* (2006.01)
*C07D 401/04* (2006.01)
*C07D 413/14* (2006.01)
*C07D 417/12* (2006.01)
*C07D 419/14* (2006.01)

(52) U.S. Cl. .................... 514/317; 514/231.5; 514/256; 514/336; 514/345; 514/376; 514/392; 514/424; 546/216; 546/261; 544/106; 544/298; 548/243; 548/300.7; 548/311.1; 548/517

(58) Field of Classification Search ............... 548/300.7, 548/243, 311.1, 517; 514/231.5, 256, 317, 514/336, 345, 376, 392, 424, 393; 546/216, 546/261; 544/106, 298
See application file for complete search history.

(56) References Cited

FOREIGN PATENT DOCUMENTS

| WO | WO-03/026652 | 4/2003 |
|---|---|---|
| WO | WO-2005-032468 | 4/2005 |
| WO | WO -2005/032468 A2 * | 4/2005 |
| WO | WO-2006/002099 | 1/2006 |

OTHER PUBLICATIONS

Agustin Casimiro-Garcia, et al.: "Expert Opinion on Therapeutic Patents," vol. 16. No. 2, Feb. 2006, pp. 119-145.
M. L. Quan et al.: "The Race to an Orally Active Factor Xa Inhibitor: Recent Advances," Current Opinion in Drug Discovery & Development, 2004, pp. 460-469.
J. Ruef et al.: "New Antithrombotic Drugs on the Horizon," Expert Opinion Investigational Drugs, 2003, pp. 781-797.
J. M. Walenga et al.: "Factor Xa Inhibitors: Today and Beyond," Current Opinion in Investigational Drugs, 2003, pp. 272-281.
L-A. Linkins et al.: "New anticoagulant Therapy," Annu. Rev. Med., 2005, pp. 63-77.
U.J. Ries et al..: "Serine Proteases as Targets for Antitrombotic Therapy," Drugs of the Future, 2003, pp. 355-370.
H. A. Wieland et al.: "Approaches in Anticoagulation: Rationales for Target Positioning," Current Opinion in Investigational Drugs, 2003, pp. 264-271.
S.A.V. Raghavan et al.: "Recent Advances in the Status and Targets of Antithrombotic Agents," Drugs of the Future, 2002, pp. 669-683.
J. Hauptmann et al.: "Synthetic Inhibitor of Thrombin and Factor XA: From Bench to Bedside," Thrombosis Reseach, 1999, pp. 203-241.
P.S. Wells et al.: "Interactions of Warfarin with Drugs and Food," American College of Physicians, 1994, pp. 676-683.
J. Ansell et al.: "Managing Oral Anticogulant Therapy," Chest, 2001, pp. 22S-38S.
J. Hirsh et al.: "Oral Anticoagulants; Mechanism of Action, clinical Effectiveness, and Optimal therapeutic Range," Chest, 2001, pp. 8S-21S.
"Heparin," Georg Thieme Verlag, Stuttgart, Romp Lexicon Chemie, Version 1.5, 1998, pp. 1-3.
Pschyrembel, Klinisches Worterbuch: "Heparin," Walter de Gruyter, 257, 1994, pp. 610.

* cited by examiner

*Primary Examiner* — Joseph K. McKane
*Assistant Examiner* — Janet L Coppins
(74) *Attorney, Agent, or Firm* — Karen B. King

(57) ABSTRACT

The invention relates to aryl-substituted heterocycles, to processes for their preparation, to their use for the treatment and/or prophylaxis of diseases and to their use for preparing medicaments for the treatment and/or prophylaxis of diseases, in particular of thromboembolic disorders.

14 Claims, No Drawings

ARYL-SUBSTITUTED HETEROCYCLES, AND USE THEREOF

RELATED APPLICATIONS/PATENTS AND INCORPORATION BY REFERENCE

This application is a National Stage Application filed under 35 U.S.C. §371 based on International Application No. PCT/EP2007/004693, filed May 25, 2007, which claims priority to German Patent Application Number 102006025314.0, filed May 31, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The invention relates to novel aryl-substituted heterocycles, to processes for their preparation, to their use for the treatment and/or prophylaxis of diseases and to their use for preparing medicaments for the treatment and/or prophylaxis of diseases, in particular of thromboembolic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin. Subsequent crosslinking of the fibrin monomers causes formation of blood clots and thus haemostasis. In addition, thrombin is a potent effector of platelet aggregation which likewise contributes significantly to haemostasis.

Haemostasis is subject to a complex regulatory mechanism. Uncontrolled activation of the coagulant system or defective inhibition of the activation processes may cause formation of local thrombi or embolisms in vessels (arteries, veins, lymph vessels) or in heart cavities. This may lead to serious thromboembolic disorders. In addition, in the case of consumption coagulopathy, hypercoagulability may—systemically—result in disseminated intravascular coagulation. Thromboembolic complications furthermore occur in microangiopathic haemolytic anaemias, extracorporeal blood circulation, such as haemodialysis, and also in connection with prosthetic heart valves.

Thromboembolic disorders are the most frequent cause of morbidity and mortality in most industrialized countries [Heart Disease: A Textbook of Cardiovascular Medicine, Eugene Braunwald, 5th edition, 1997, W.B. Saunders Company, Philadelphia].

The anticoagulants, i.e. substances for inhibiting or preventing blood coagulation, which are known from the prior art, have various, often grave disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally or subcutaneously. Owing to more favourable pharmacokinetic properties, preference is nowadays more and more given to low-molecular-weight heparin; however, even with low-molecular-weight heparin, it is not possible to avoid the known disadvantages described below, which are involved in heparin therapy. Thus, heparin is ineffective when administered orally and has a relatively short half-life. Since heparin inhibits a plurality of factors of the blood coagulation cascade at the same time, the action is non-selective. Moreover, there is a high risk of bleeding; in particular, brain haemorrhages and gastrointestinal bleeding may occur, which may result in thrombopenia, drug-induced alopecia or osteoporosis [Pschyrembel, Klinisches Worterbuch, 257th edition, 1994, Walter de Gruyter Verlag, page 610, entry "Heparin"; Römpp Lexikon Chemie, Version 1.5, 1998, Georg Thieme Verlag Stuttgart, entry "Heparin"].

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a non-selective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required [J. Hirsh, J. Dalen, D. R. Anderson et al., "Oral anticoagulants: Mechanism of action, clinical effectiveness, and optimal therapeutic range" *Chest* 2001, 119, 8S-21S; J. Ansell, J. Hirsh, J. Dalen et al., "Managing oral anticoagulant therapy" *Chest* 2001, 119, 22S-38S; P. S. Wells, A. M. Holbrook, N. R. Crowther et al., "Interactions of warfarin with drugs and food" *Ann. Intern. Med.* 1994, 121, 676-683].

Recently, a novel therapeutic approach for the treatment and prophylaxis of thromboembolic disorders has been described. This novel therapeutic approach aims to inhibit factor Xa. Because of the central role which factor Xa plays in the blood coagulation cascade, factor Xa is one of the most important targets for anticoagulants [J. Hauptmann, J. Sturzebecher, *Thrombosis Research* 1999, 93, 203; S. A. V. Raghavan, M. Dikshit, "Recent advances in the status and targets of antithrombotic agents" *Drugs Fut.* 2002, 27, 669-683; H. A. Wieland, V. Laux, D. Kozian, M. Lorenz, "Approaches in anticoagulation: Rationales for target positioning" *Curr. Opin. Investig. Drugs* 2003, 4, 264-271; U. J. Ries, W. Wienen, "Serine proteases as targets for antithrombotic therapy" *Drugs Fut.* 2003, 28, 355-370; L.-A. Linkins, J. I. Weitz, "New anticoagulant therapy" *Annu. Rev. Med.* 2005, 56, 63-77 (online publication August 2004)].

It has been shown that, in animal models, various both peptidic and nonpeptidic compounds are effective as factor Xa inhibitors. A large number of direct factor Xa inhibitors is already known [J. M. Walenga, W. P. Jeske, D. Hoppensteadt, J. Fareed, "Factor Xa Inhibitors: Today and beyond" *Curr. Opin. Investig. Drugs* 2003, 4, 272-281; J. Ruef, H. A. Katus, "New antithrombotic drugs on the horizon" *Expert Opin. Investig. Drugs* 2003, 12, 781-797; M. L. Quan, J. M. Smallheer, "The race to an orally active Factor Xa inhibitor: Recent advances" *Curr. Opin. Drug Discovery & Development* 2004, 7, 460-469; A. Casimiro-Garcia et al., "Progress in the discovery of Factor Xa inhibitors" *Expert Opin. Ther. Patents*

2006, 15, 119-145]. Nonpeptidic low-molecular-weight factor Xa inhibitors are also described, for example, in WO 06/002099 and WO 03/026652.

It is an object of the present invention to provide novel alternative compounds having a comparable or improved activity for controlling disorders, in particular thromboembolic disorders, in humans and animals.

The invention provides compounds of the formula

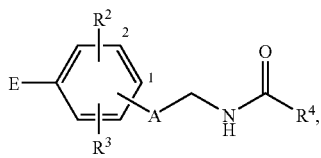

(I)

in which
E represents a group of the formula

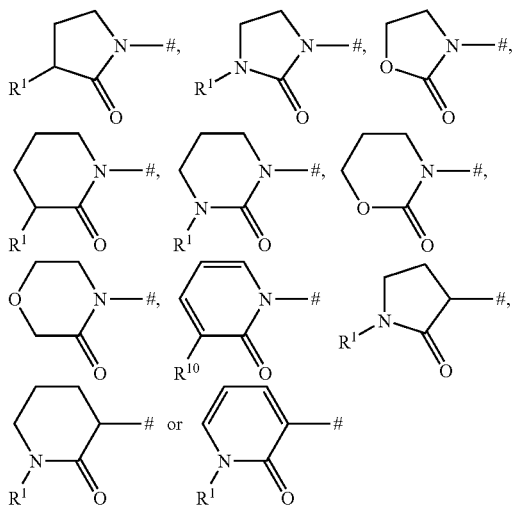

where
# is the point of attachment to the phenyl ring,
$R^1$ represents hydrogen, hydroxy, amino, $C_1$-$C_4$-alkyl, $C_1$-$C_4$-alkoxy, $C_1$-$C_4$-alkylamino, $C_3$-$C_6$-cycloalkyl, $C_3$-$C_6$-cycloalkyloxy, $C_3$-$C_6$-cycloalkylamino, $C_1$-$C_4$-alkylcarbonylamino or $C_1$-$C_4$-alkoxycarbonylamino,
where
alkyl, alkoxy, alkylamino may be substituted by a substituent, the substituent being selected from the group consisting of hydroxy, amino, $C_1$-$C_4$-alkoxy, $C_1$-$C_4$-alkylamino, $C_3$-$C_6$-cycloalkylamino and a 4- to 7-membered saturated heterocyclyl bound via an N atom which may contain a ring member from the group consisting of N—$R^5$ or O,
where
$R^5$ represents hydrogen or $C_1$-$C_4$-alkyl,
and
$R^{10}$ represents hydrogen, $C_1$-$C_4$-alkyl, $C_1$-$C_4$-alkoxy, $C_3$-$C_6$-cycloalkyl, $C_3$-$C_6$-cycloalkyloxy or —$NR^{11}R^{12}$,
where
$R^{11}$ represents $C_1$-$C_4$-alkyl or $C_3$-$C_6$-cycloalkyl,
and
$R^{12}$ represents $C_1$-$C_4$-alkyl, A represents a 5-membered heteroaryl or partially unsaturated 5-membered heterocyclyl,
where heteroaryl and heterocyclyl are attached in the 1- or 2-position to the phenyl ring and heteroaryl and heterocyclyl for their part have a 1,3-attachment to the phenyl ring and the carbonylaminomethyl group,
and
where heteroaryl and heterocyclyl are substituted by a substituent $R^6$,
where $R^6$ is attached to the neighbouring atom of the atom to which the carbonylaminomethyl group is attached and has a 1,4-attachment to the phenyl ring
and
where the atom to which $R^6$ is attached is a nitrogen or carbon atom
and
where
$R^6$ represents phenyl or 5- or 6-membered heteroaryl,
where phenyl and heteroaryl may be substituted by 1 to 3 substituents, where the substituents independently of one another are selected from the group consisting of halogen, hydroxyl, hydroxymethyl, hydroxyethyl, amino, aminomethyl, aminoethyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, hydroxycarbonyl, hydroxycarbonylmethyl, aminocarbonyl, aminocarbonylmethyl, $C_1$-$C_4$-alkoxycarbonyl, $C_1$-$C_4$-alkoxycarbonylmethyl, $C_1$-$C_4$-alkylaminocarbonyl, $C_1$-$C_4$-alkylaminocarbonylmethyl, aminosulphonyl, $C_1$-$C_4$-alkylaminosulphonyl and $C_1$-$C_4$-alkylsulphonyl,
$R^2$ represents hydrogen, fluorine, chlorine, cyano, hydroxy, amino, trifluoromethyl, trifluoromethoxy, $C_1$-$C_4$-alkyl, $C_1$-$C_4$-alkoxy, $C_1$-$C_4$-alkoxymethyl, $C_1$-$C_4$-alkylamino, $C_3$-$C_6$-cycloalkyl, aminocarbonyl, $C_1$-$C_4$-alkoxycarbonyl or $C_1$-$C_4$-alkylaminocarbonyl,
$R^3$ represents hydrogen, fluorine, chlorine, cyano, hydroxy, amino, trifluoromethyl, trifluoromethoxy, $C_1$-$C_4$-alkyl, $C_1$-$C_4$-alkoxy, $C_1$-$C_4$-alkoxymethyl, $C_1$-$C_4$-alkylamino, $C_3$-$C_6$-cycloalkyl, aminocarbonyl, $C_1$-$C_4$-alkoxycarbonyl or $C_1$-$C_4$-alkylaminocarbonyl,
$R^4$ represents a group of the formula

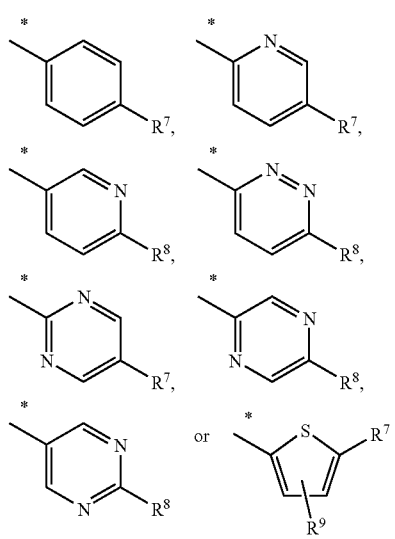

where

* is the point of attachment to the carbonyl group, $R^7$ represents hydrogen, fluorine, chlorine, cyano, ethynyl, $C_1$-$C_4$-alkyl, $C_1$-$C_4$-alkoxy or $C_3$-$C_6$-cycloalkyl, $R^8$ represents hydrogen, amino, $C_1$-$C_4$-alkyl, $C_1$-$C_4$-alkylamino or $C_3$-$C_6$-cycloalkyl, and $R^9$ represents hydrogen, fluorine, chlorine, amino or $C_1$-$C_4$-alkyl, and their salts, their solvates and the solvates of their salts.

Compounds according to the invention are the compounds of the formula (I) and their salts, solvates and solvates of the salts, the compounds, comprised by formula (I), of the formulae mentioned below and their salts, solvates and solvates of the salts and the compounds, comprised by formula (I), mentioned below as embodiments and their salts, solvates and solvates of the salts if the compounds, comprised by formula (I), mentioned below are not already salts, solvates and solvates of the salts.

Depending on their structure, the compounds according to the invention can exist in stereoisomeric forms (enantiomers, diastereomers). Accordingly, the invention comprises the enantiomers or diastereomers and their respective mixtures. From such mixtures of enantiomers and/or diastereomers, it is possible to isolate the stereoisomerically uniform components in a known manner.

If the compounds according to the invention can be present in tautomeric forms, the present invention comprises all tautomeric forms.

In the context of the present invention, preferred salts are physiologically acceptable salts of the compounds according to the invention. The invention also comprises salts which for their part are not suitable for pharmaceutical applications, but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds according to the invention which, in solid or liquid state, form a complex by coordination with solvent molecules. Hydrates are a specific form of the solvates where the coordination is with water. In the context of the present invention, preferred solvates are hydrates.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In the context of the present invention, unless specified differently, the substituents have the following meanings:

Alkyl per se and "alk" and "alkyl" in alkoxy alkylamino, alkoxycarbonyl alylaminocarbonyl alkylaminosulphonyl and alkylsulphonyl represents a straight-chain or branched alkyl radical having generally 1 to 4, preferably 1 or 2, carbon atoms, by way of example and by way of preference methyl, ethyl, n-propyl, isopropyl and tert-butyl.

By way of example and by way of preference, alkoxy represents methoxy, ethoxy, n-propoxy, isopropoxy and tert-butoxy.

Alkylamino represents an alkylamino radical having one or two alkyl substituents (selected independently of one another), by way of example and by preference methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methyl-amino. By way of example, $C_1$-$C_3$-alkylamino represents a monoalkylamino radical having 1 to 3 carbon atoms or represents a dialkylamino radical having in each case 1 to 3 carbon atoms per alkyl substituent.

By way of example and by way of preference alkoxycarbonyl represents methoxycarbonyl, ethoxycarbonyl, n-propoxycarbonyl, isopropoxycarbonyl and tert-butoxycarbonyl.

Alkylaminocarbonyl represents an alkylaminocarbonyl radical having one or two alkyl substituents (selected independently of one another), by way of example and by way of preference methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. By way of example, $C_1$-$C_3$-alkylaminocarbonyl represents a monoalkylaminocarbonyl radical having 1 to 3 carbon atoms or represents a dialkylaminocarbonyl radical having in each case 1 to 3 carbon atoms per alkyl substituent.

Alkylaminosulphonyl represents an alkylaminosulphonyl radical having one or two alkyl substituents (selected independently of one another), by way of example and by way of preference methylaminosulphonyl, ethylaminosulphonyl, n-propylaminosulphonyl, isopropylaminosulphonyl, tert-butylaminosulphonyl, N,N-dimethylaminosulphonyl, N,N-diethylaminosulphonyl, N-ethyl-N-methylaminosulphonyl, N-methyl-N-n-propylaminosulphonyl, N-isopropyl-N-n-propylaminosulphonyl and N-tert-butyl-N-methylaminosulphonyl. By way of example, $C_1$-$C_3$-alkylaminosulphonyl represents a monoalkylaminosulphonyl radical having 1 to 3 carbon atoms or represents a dialkylaminosulphonyl radical having in each case 1 to 3 carbon atoms per alkyl substituent.

By way of example and by way of preference alkylsulphonyl represents methylsulphonyl, ethylsulphonyl, n-propylsulphonyl, isopropylsulphonyl and tert-butylsulphonyl.

Cycloalkyl represents a cycloalkyl group having generally 3 to 6 carbon atoms, preferably 3 to 5 carbon atoms, by way of example and by way of preference cyclopropyl, cyclobutyl, cyclopentyl and cyclohexyl.

Heterocyclyl, when not further restricted, represents a monocyclic radical having 4 to 7 ring atoms and up to 3, preferably up to 2, heteroatoms and/or heterogroups from the group consisting of N, O, S, SO, $SO_2$. The heterocyclyl radicals can be saturated or partially unsaturated. Preference is given to 5-membered monocyclic heterocyclyl radicals having up to two heteroatoms from the group consisting of O, N and S, such as, by way of example and by way of preference, tetrahydrofuranyl, pyrrolidinyl, pyrrolinyl, isoxazolinyl and pyrazolinyl.

Heteroaryl represents an aromatic monocyclic radical having 5 ring atoms and up to 4 heteroatoms from the group consisting of S, O and N, by way of example and by way of preference thienyl, furyl, pyrrolyl, thiazolyl, oxazolyl, isoxazolyl, isothiazolyl, imidazolyl and pyrazolyl.

If radicals in the compounds according to the invention are substituted, the radicals can, unless specified otherwise, be mono- or polysubstituted. In the context of the present invention, the meanings of all radicals which occur more than once are independent of one another. Substitution with one, two or three identical or different substituents is preferred. Very particular preference is given to substitution with one substituent.

In the formulae of the group which may represent $R^4$, the end point of the line next to a * does not represent a carbon atom or a $CH_2$ group, but is part of the bond to the atom to which $R^4$ is attached.

In the formulae of the group which may represent E, the end point of the line next to a # does not represent a carbon atom or a $CH_2$ group, but is part of the bond to the atom to which E is attached.

Preference is given to compounds of the formula (I), in which
E represents a group of the formula

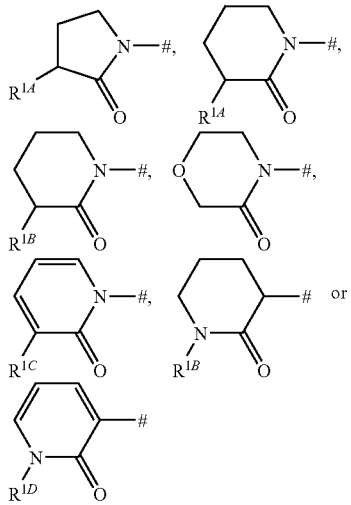

where
# is the point of attachment to the phenyl ring,
$R^{1A}$ represents hydrogen, hydroxy, hydroxymethyl, 2-hydroxyethyl, amino or methoxy,
$R^{1B}$ represents hydrogen, hydroxy, amino, methyl or ethyl,
where
methyl may be substituted with pyrrolidin-1-yl,
and
ethyl may be substituted by a substituent, the substituent being selected from the group consisting of hydroxy, amino, diethylamino and cyclopropylamino,
$R^{1C}$ represents hydrogen, methyl or ethyl,
where
methyl may be substituted by a substituent, the substituent being selected from the group consisting of hydroxy and pyrrolidin-1-yl,
and
ethyl may be substituted by a substituent, the substituent being selected from the group consisting of hydroxy, amino and cyclopropylamino,
and
$R^{1D}$ represents hydrogen, methyl or ethyl,
in which
methyl may be substituted by a substituent, where the substituent is selected from the group consisting of cyclopropylamino and pyrrolidin-1-yl,
and
ethyl may be substituted by a substituent, where the substituent is selected from the group consisting of hydroxy, amino and cyclopropylamino,
A represents a 5-membered heteroaryl or partially unsaturated 5-membered heterocyclyl,
where heteroaryl and heterocyclyl are attached in the 1- or 2-position to the phenyl ring and heteroaryl and heterocyclyl for their part have a 1,3-attachment to the phenyl ring and the carbonylaminomethyl group,
and
where heteroaryl and heterocyclyl are substituted by a substituent $R^6$,
where $R^6$ is attached to the neighbouring atom of the atom to which the carbonylaminomethyl group is attached and has a 1,4-attachment to the phenyl ring
and
where the atom to which $R^6$ is attached is a nitrogen or carbon atom
and
where
$R^6$ represents phenyl or a 5- or 6-membered heteroaryl, where phenyl and heteroaryl may be substituted by 1 to 3 substituents, where the substituents independently of one another are selected from the group consisting of halogen, hydroxy, amino, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, hydroxycarbonyl, hydroxycarbonylmethyl, aminocarbonyl, aminocarbonylmethyl, $C_1$-$C_4$-alkoxycarbonyl, $C_1$-$C_4$-alkoxycarbonylmethyl, $C_1$-$C_4$-alkylaminocarbonyl, $C_1$-$C_4$-alkylaminocarbonylmethyl, aminosulphonyl, $C_1$-$C_4$-alkylaminosulphonyl and $C_1$-$C_4$-alkylsulphonyl,
$R^2$ represents hydrogen, fluorine, chlorine, cyano, hydroxy, $C_1$-$C_4$-alkyl or $C_1$-$C_4$-alkoxy,
$R^3$ represents hydrogen, fluorine, chlorine, cyano, hydroxy, $C_1$-$C_4$-alkyl, $C_1$-$C_4$-alkoxy, $C_1$-$C_4$-alkoxymethyl, cyclopropyl, aminocarbonyl, $C_1$-$C_4$-alkoxycarbonyl or $C_1$-$C_4$-alkylaminocarbonyl,
$R^4$ represents a group of the formula

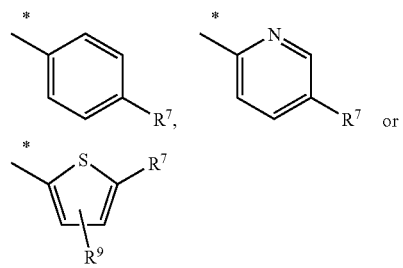

where
* is the point of attachment to the carbonyl group,

R⁷ represents fluorine, chlorine, ethynyl, methyl or methoxy,
and
R⁹ represents hydrogen,
and their salts, their solvates and the solvates of their salts.

Preference is also given to compounds of the formula (I), in which
E represents a group of formula where
\# is the point of attachment to the phenyl ring,
A represents pyrazolyl, oxadiazolyl or isoxazolinyl,
  where pyrazolyl, oxadiazolyl and isoxazolinyl are attached in the 1-position to the phenyl ring and pyrazolyl, oxadiazolyl and isoxazolinyl for their part have a 1,3-attachment to the phenyl ring and the carbonylaminomethyl group,
  and
  where pyrazolyl, oxadiazolyl and isoxazolinyl are substituted by a substituent $R^6$,
    where $R^6$ is attached to the neighbouring atom of the atom to which the carbonylaminomethyl group is attached and has a 1,4-attachment to the phenyl ring and
    where the atom to which $R^6$ is attached is a nitrogen or carbon atom
    and
    where
    $R^6$ represents phenyl, pyrid-2-yl, pyrid-3-yl, pyrid-4-yl, 1,3-oxazol-2-yl or pyrimidin-2-yl,
      where phenyl, pyrid-2-yl, pyrid-3-yl, pyrid-4-yl, 1,3-oxazol-2-yl and pyrimidin-2-yl may be substituted by 1 to 3 substituents, where the substituents independently of one another are selected from the group consisting of halogen, hydroxy, amino, $C_1$-$C_4$-alkyl, $C_1$-$C_4$-alkoxy, $C_1$-$C_4$-alkylamino, hydroxycarbonyl, aminocarbonyl, $C_1$-$C_4$-alkoxycarbonyl, $C_1$-$C_4$-alkylaminocarbonyl, aminosulphonyl, $C_1$-$C_4$-alkylaminosulphonyl and $C_1$-$C_4$-alkylsulphonyl,
$R^2$ represents hydrogen or fluorine,
$R^3$ represents hydrogen, fluorine, chlorine, cyano, methyl, ethyl, n-propyl, isopropyl, methoxy, ethoxy, methoxymethyl or cyclopropyl,
$R^4$ represents a group of the formula where
\* is the point of attachment to the carbonyl group,
$R^7$ represents fluorine, chlorine or methyl,
and
$R^9$ represents hydrogen,
and their salts, their solvates and the solvates of their salts.

Preference is also given to compounds of the formula (I) in which
E represents a group of the formula where
\# is the point of attachment to the phenyl ring,
A represents pyrazolyl, oxadiazolyl or isoxazolinyl,
  where pyrazolyl, oxadiazolyl and isoxazolinyl are attached in the 1-position to the phenyl ring and pyrazolyl, oxadiazolyl and isoxazolinyl for their part have a 1,3-attachment to the phenyl ring and the carbonylaminomethyl group,
  and where pyrazolyl, oxadiazolyl and isoxazolinyl are substituted by a substituent $R^6$, where $R^6$ is attached to the neighbouring atom of the atom to which the carbonylaminomethyl group is attached and has a 1,4-attachment to the phenyl ring and where the atom to which $R^6$ is attached is a nitrogen or carbon atom
and
where $R^6$ represents phenyl, pyrid-2-yl, pyrid-3-yl, pyrid-4-yl, where phenyl, pyrid-2-yl, pyrid-3-yl and pyrid-4-yl may be substituted by a substituent, the substituent being selected from the group consisting of halogen, hydroxy, amino, $C_1$-$C_4$-alkyl, $C_1$-$C_4$-alkoxy, $C_1$-$C_4$-alkylamino, hydroxycarbonyl, aminocarbonyl, $C_1$-$C_4$-alkoxycarbonyl, and $C_1$-$C_4$-alkylaminocarbonyl, $R^2$ represents hydrogen or fluorine, $R^3$ represents hydrogen, fluorine, chlorine, methyl or methoxy, $R^4$ represents a group of the formula in which
* is the point of attachment to the carbonyl group,
$R^7$ represents chlorine,
and
$R^9$ represents hydrogen,
and their salts, their solvates and the solvates of their salts.

Preference is also given to compounds of the formula (I) in which E represents a group of the formula where # is the point of attachment to the phenyl ring.

Preference is also given to compounds of the formula (I) in which E represents a group of the formula where # is the point of attachment to the phenyl ring.

Preference is also given to compounds of the formula (I) in which A represents pyrazolyl, oxadiazolyl or isoxazolinyl.

Preference is also given to compounds of the formula (I) in which A represents pyrazolyl.

Preference is also given to compounds of the formula (I) in which $R^6$ represents pyridyl, 4-fluorophenyl or 4-methoxyphenyl.

Preference is also given to compounds of the formula (I) in which $R^2$ represents hydrogen or fluorine.

Preference is also given to compounds of the formula (I) in which $R^3$ represents hydrogen, fluorine, chlorine, methyl or methoxy.

Preference is also given to compounds of the formula (I) in which $R^3$ represents hydrogen.

Preference is also given to compounds of the formula (I) in which $R^2$ and $R^3$ represent hydrogen.

Preference is also given to compounds of the formula (I) in which $R^2$ represents hydrogen and $R^3$ represents fluorine.

Preference is also given to compounds of the formula (I) in which $R^4$ represents a group of the formula where * is the point of attachment to the carbonyl group, $R^7$ represents chlorine and $R^9$ represents hydrogen.

The individual radical definitions given in the respective combinations or preferred combinations of radicals are, independently of the particular given combinations of radicals, also replaced by any radical definitions of other combinations.

Very particular preference is given to combinations of two or more of the preferred ranges mentioned above.

The invention furthermore provides a process for preparing the compounds of the formula (I), or their salts, their solvates or the solvates of their salts, wherein compounds of the formula (II)

in which A, $R^2$, $R^3$ and $R^4$ have the meaning given above, are reacted with compounds of the formula

E—H (III), in which E has the meaning given above.

For compounds of the formula (III) in which the hydrogen shown in formula (III) is attached to E via a nitrogen atom, the reaction is generally carried out in inert solvents with addition of a copper(I) salt, a base and a diamine ligand, preferably in a temperature range of from 60° C. to reflux of the solvent at atmospheric pressure.

Inert solvents are, for example, aprotic solvents, such as toluene, dioxane, tetrahydrofuran or dimethylformamide; preference is given to dioxane.

Copper(I) salts are, for example, copper(I) iodide, copper (I) chloride or copper(I) oxide; preference is given to copper (I) iodide.

Bases are, for example, potassium phosphate, potassium carbonate or caesium carbonate; preference is given to potassium phosphate.

Diamine ligands are, for example, 1,2-diamines, such as N,N'-dimethylethylenediamine.

For compounds of the formula (III) in which the hydrogen shown in formula (III) is attached via a carbon atom to E, the reaction is generally carried out in inert solvents, initially with addition of a strong base, then addition of a zinc salt and finally addition of a compound of the formula (II) and a palladium complex. The first two partial steps, the reaction with the strong base and the reaction with the zinc salt, are preferably carried out in a temperature range of from −30 to 0° C.; the last partial step is preferably carried out at from room temperature to the boiling point of the solvent.

Inert solvents are, for example, ethers, such as tetrahydrofuran, dioxane or 1,2-dimethoxyethane; if appropriate as a mixture with hydrocarbons, such as, for example, hexane. Preference is given to tetrahydrofuran.

Strong bases are, for example, sec-butyllithium, tert-butyllithium, lithium diisopropylamide or lithium hexamethyldisilazide. Preference is given to sec-butyllithium.

The preferred zinc salt is zinc chloride.

Palladium complexes are formed in situ from palladium compounds and ligands. Suitable palladium compounds are, for example, palladium(II) acetate, palladium(II) chloride, bis(triphenylphosphine)palladium(II) chloride, tetrakis(triophenylphosphine)palladium(0), bis(dibenzylideneacetone)palladium(0). Preference is given to bis(dibenzylidene-acetone)palladium(0). Suitable ligands are, for example 2-dicyclohexylphosphino-2'-(N,N-dimethylamino) biphenyl, binaphthyl or N-heterocyclic carbene ligands. Preference is given to 2-dicyclohexylphosphino-2'-(N,N-dimethylamino)biphenyl.

The compounds of the formula (III) are known and can be synthesized by known methods from the appropriate starting materials.

The compounds of the formula (II) are known or can be prepared by reacting compounds of the formula

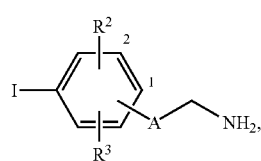

(IV)

in which A, $R^2$ and $R^3$ have the meaning given above, with compounds of the formula

(V)

in which $R^4$ has the meaning given above, and
$X^1$ represents halogen, preferably bromine or chlorine, or hydroxy.

If $X^1$ represents halogen, the reaction is generally carried out in inert solvents, if appropriate in the presence of a base, preferably in a temperature range of from −30° C. to 50° C. at atmospheric pressure.

Inert solvents are, for example, tetrahydrofuran, methylene chloride, pyridine, dioxane or dimethylformamide; preference is given to pyridine, tetrahydrofuran or methylene chloride.

Bases are, for example, triethylamine, diisopropylethylamine or N-methylmorpholine; preference is given to diisopropylethylamine.

If $X^1$ represents hydroxy, the reaction is generally carried out in inert solvents in the presence of a dehydrating agent, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is also possible to use mixtures of the solvents. Particular preference is given to dichloromethane or dimethylformamide.

Here, suitable dehydrating agents are, for example, carbodiimides, such as, for example, N,N'-diethyl-, N,N,'-dipropyl-, N,N'-diisopropyl-, N,N'-dicyclohexylcarbodiimide, N-(3-dimethylaminoiso-propyl)-N'-ethylcarbodiimide hydrochloride (EDC), N-cyclohexylcarbodiimide-N'-propyloxymethyl-polystyrene (PS-carbodiimide) or carbonyl compounds, such as carbonyldiimidazole, or 1,2-oxazolium compounds, such as 2-ethyl-5-phenyl-1,2-oxazolium 3-sulphate or 2-tert-butyl-5-methyl-isoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzo-triazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates, such as, for example, sodium carbonate or potassium carbonate or sodium bicarbonate or potassium bicarbonate, or organic bases, such as trialkylamines, for example triethylamine, N-methylmorpholine, N-methylpiperidine, 4-dimethyl-aminopyridine or diisopropylethylamine.

The condensation is preferably carried out with HATU or with EDC in the presence of HOBt.

The compounds of the formula (IV) are known or can be synthesized according to processes known to those skilled in the art for synthesizing the heterocycle A from the appropriate starting materials.

The compounds of the formula (V) are known or can be synthesized according to known processes from the appropriate starting materials.

If appropriate, the nitrogen of the amide in compounds of the formulae (II) and (IV) can be protected during the reaction by a protective group known to the person skilled in the art; preference is given to a 2,4-dimethoxybenzyl group which is removed under the conditions of the last step of the synthesis of the compounds of the formula (I).

The preparation of the compounds according to the invention can be illustrated by the synthesis scheme below:

The compounds according to the invention are selective inhibitors of blood coagulation factor Xa which act in particular as anticoagulants.

In addition, the compounds according to the invention have favourable physicochemical properties, such as, for example, good solubility in water and physiological media, which is advantageous for their therapeutic application.

The present invention furthermore provides the use of the compounds according to the invention for the treatment and/or prophylaxis of disorders, preferably thromboembolic disorders and/or thromboembolic complications.

Scheme

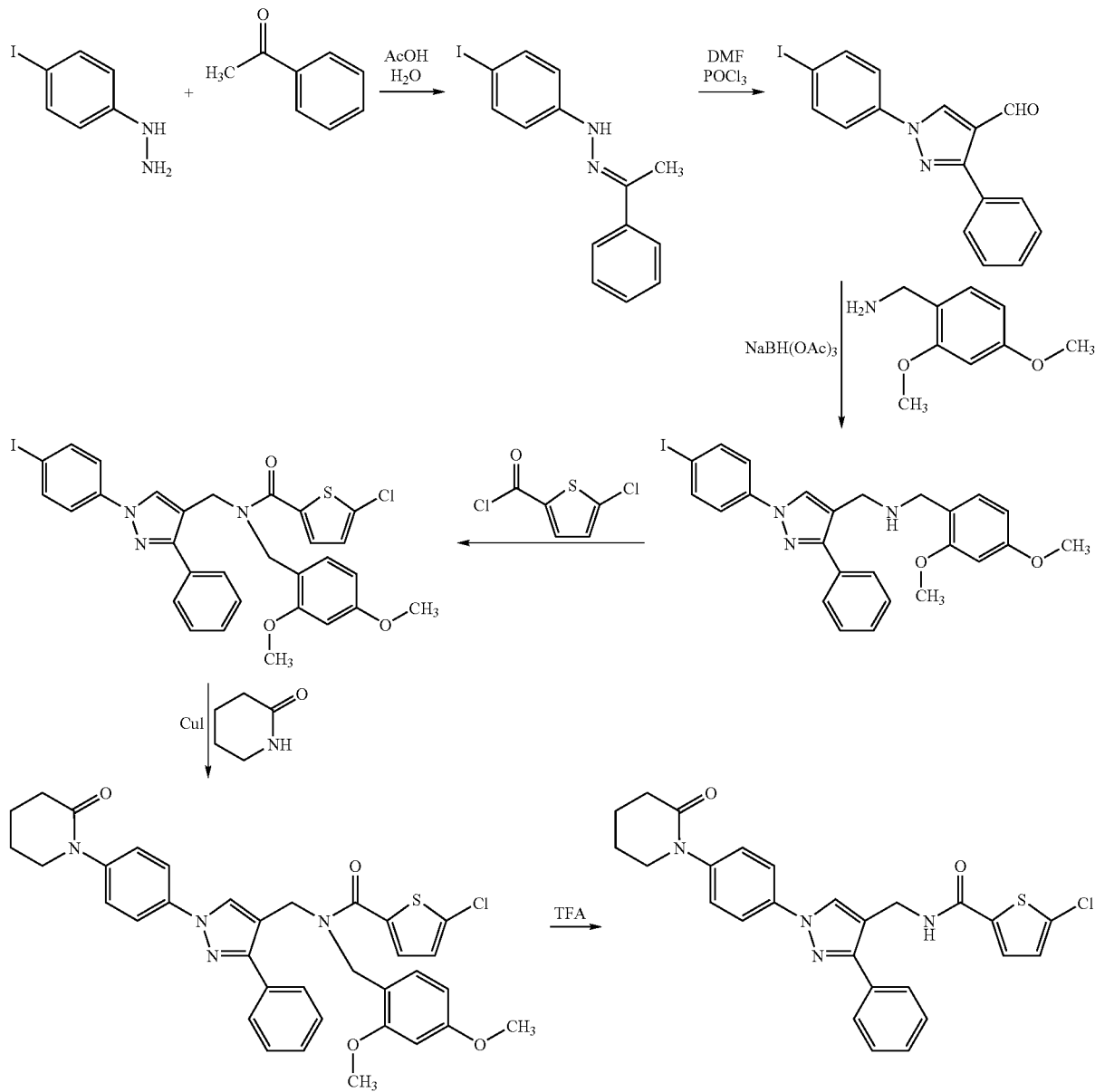

The compounds according to the invention have an unforeseeable useful pharmacological activity spectrum.

Accordingly, they are suitable for use as medicaments for the treatment and/or prophylaxis of diseases in humans and animals.

For the purposes of the present invention, "thromboembolic disorders" include in particular disorders such as ST-elevation myocardial infarction (STEMI) or non-ST-elevation myocardial infarction (non-STEMI), stable angina pectoris, unstable angina pectoris, reocclusions and restenoses after coronary interventions such as angioplasty or aortocoronary bypass, peripheral arterial occlusive diseases, pulmonary embolisms, deep vein thromboses and kidney vein thromboses, transitory ischaemic attacks and also thrombotic and thromboembolic stroke.

Accordingly, the substances are also suitable for preventing and treating cardiogenic thromboembolisms, such as, for example, brain ischaemias, stroke and systemic thromboembolisms and ischaemias, in patients having acute, intermittent or persistent cardioarrhythmias, such as, for example, atrial fibrillation, and those undergoing cardioversion, furthermore patients having heart valve disorders or having artificial heart valves. In addition, the compounds according to the invention are suitable for treating disseminated intravascular coagulation (DIC).

Thromboembolic complications furthermore occur during microangiopathic haemolytic anaemias, extracorporeal blood circulation, such as haemodialysis, and in connection with heart valve prostheses.

Moreover, the compounds according to the invention are also suitable for the prophylaxis and/or treatment of atherosclerotic vascular disorders and inflammatory disorders, such as rheumatic disorders of the locomotor apparatus, and in addition also for the prophylaxis and/or treatment of Alzheimer's disease. Moreover, the compounds according to the invention can be used for inhibiting tumour growth and formation of metastases, for microangiopathies, age-related macular degeneration, diabetic retinopathy, diabetic nephropathy and other microvascular disorders, and also for the prevention and treatment of thromboembolic complications, such as, for example, venous thromboembolisms, in tumour patients, in particular patients undergoing major surgical interventions or chemo- or radiotherapy.

The compounds according to the invention can additionally also be used for preventing coagulation ex vivo, for example for preserving blood and plasma products, for cleaning/pretreating catheters and other medical tools and instruments, for coating synthetic surfaces of medical tools and instruments used in vivo or ex vivo or for biological samples comprising factor Xa.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an anticoagulatory effective amount of the compound according to the invention.

The present invention furthermore provides a method for preventing blood coagulation in vitro, in particular in banked blood or biological samples comprising factor Xa, which method is characterized in that an anticoagulatory effective amount of the compound according to the invention is added.

The present invention furthermore provides medicaments comprising a compound according to the invention and one or more further active compounds, in particular for the treatment and/or prophylaxis of the disorders mentioned above. The following compounds may be mentioned by way of example and by way of preference as active compounds suitable for combinations:

lipid-lowering agents, in particular HMG-CoA (3-hydroxy-3-methylglutaryl-coenzyme A) reductase inhibitors;

coronary therapeutics/vasodilators, in particular ACE (angiotensin converting enzyme) inhibitors; AII (angiotensin II) receptor antagonists; β-adrenoceptor antagonists; alpha-1-adrenoceptor antagonists; diuretics; calcium channel blockers; substances which cause an increase in the cyclic guanosine monophosphate (cGMP) concentration such as, for example, stimulators of soluble guanylate cyclase;

plasminogen activators (thrombolytics/fibrinolytics) and compounds enhancing thrombolysis/fibrinolysis, such as inhibitors of the plasminogen activator inhibitor (PAI inhibitors) or inhibitors of the thrombin-activated fibrinolysis inhibitor (TAFI inhibitors);

anticoagulants;

platelet aggregation inhibiting substances (platelet aggregation inhibitors, thrombocyte aggregation inhibitors);

fibrinogen receptor antagonists (glycoprotein-IIb/IIIa antagonists);

and also antiarrhythmics.

The present invention furthermore provides medicaments comprising at least one compound according to the invention, usually together with one or more inert non-toxic pharmaceutically acceptable auxiliaries, and their use for the purposes mentioned above.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the compounds according to the invention in suitable administration forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbarly) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Preference is given to oral or parenteral administration, in particular oral administration.

The compounds according to the invention can be converted into the stated administration forms. This can take place in a manner known per se by mixing with inert, non-toxic, pharmaceutically suitable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

In general, it has proved advantageous to administer on parenteral administration amounts of from about 0.001 to 1 mg/kg, preferably from about 0.01 to 0.5 mg/kg, of body weight to achieve effective results. The dosage on oral administration is from about 0.01 to 100 mg/kg, preferably about 0.01 to 20 mg/kg, and very particularly preferably 0.1 to 10 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The invention is illustrated by the working examples below. The invention is not limited to the examples.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

Abbreviations

TLC Thin-Layer Chromatography
DCI Direct Chemical Ionization (in MS)
DMF N,N-Dimethylformamide
DMSO Dimethyl sulphoxide
d day(s)
ee Enantiomeric excess
eq. Equivalent(s)
ESI Electrospray Ionization (in MS)
h hour(s)
HPLC High-Pressure, High-Performance Liquid Chromatography
LC-MS Liquid Chromatography-coupled Mass Spectroscopy
min minute(s)
MS Mass Spectroscopy
NMR Nuclear Magnetic Resonance spectroscopy
RP Reversed Phase (in HPLC)
RT Room Temperature
$R_t$ Retention time (in HPLC)
TBTU O-(benzotriazol-1-yl)-N,N,N',N'-tetramethyluronium tetrafluoroborate
THF Tetrahydrofuran
LC-MS and HPLC Methods Method 1: Instrument: HP 1100 with DAD detection; column: Kromasil 100 RP-18, 60 mm×2.1 mm, 3.5 μm; mobile phase A: 5 ml of perchloric acid (70% strength)/1 of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 mumin; column temperature: 30° C.; UV detection: 210 nm.

Method 2: Instrument: HP 1100 with DAD detection; column: Kromasil 100 RP-18, 60 mm×2.1 mm, 3.5 μm; mobile phase A: 5 ml of perchloric acid (70% strength)/1 of water, mobile phase B: acetonitrile; gradient: 0 min 2% B→0.5 min 2% B→4.5 min 90% B→9 min 0% B→9.2 min 2% B→10 min 2% B; flow rate: 0.75 mumin; column temperature: 30° C.; UV detection: 210 nm.

Method 3: MS instrument type: Micromass ZQ; HPLC instrument type: Waters Alliance 2795; Column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; Gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4: MS instrument type: Micromass ZQ; HPLC instrument type: HP 1100 Series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 5: Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 6: column: GROM-SIL 120 ODS-4 HE, 10 μM, 250 mm×30 mm; mobile phase and gradient program: acetonitrile/0.1% strength aqueous formic acid 10:90 (0-3 min), acetonitrile/0.1% strength aqueous formic acid 10:90→95:5 (3-27 min), acetonitrile/0.1% strength aqueous formic acid 95:5 (27-34 min), acetonitrile/0.1% strength aqueous formic acid 10:90 (34-38 min); flow rate: 50 ml/min; temperature: 22° C.; UV detection: 254 nm.

Starting Materials

Example 1A

Acetophenone-(4-iodophenyl)hydrazone

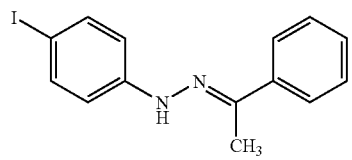

A solution of 1.54 g (12.82 mmol) of acetophenone in 10 ml of 50% strength acetic acid is added to a solution of 2.0 g (8.546 mmol) of 4-iodophenylhydrazine in 30 ml of the same solvent. The mixture is stirred at room temperature, and a precipitate is formed. After 30 minutes, the precipitate is filtered off and thoroughly washed with water and then with cyclohexane. The residue is dried under high vacuum. This gives 1.95 g (68% of theory) of the title compound.

$^1$H-NMR (400 MHz, DMSO-$d_6$, δ/ppm): 7.78 (d, 2H), 7.51 (d, 2H), 7.38 (dd, 2H), 7.30 (dd, 1H), 7.07 (d, 2H), 2.25 (s, 3H).

HPLC (Method 4): $R_t$=3.22 min.

MS (ESIpos, m/z): 337 (M+H)$^+$.

Example 2A 1-(4-Iodophenyl)-3-phenyl-1H-pyrazole-4-carbaldehyde

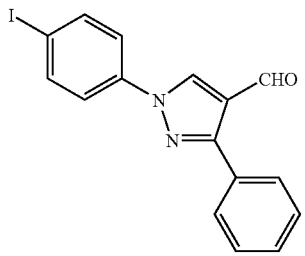

At 0° C., 1.08 ml (11.58 mmol) of phosphoryl chloride (POCl$_3$) are slowly added dropwise to 10 ml of anhydrous N,N-dimethylformamide. After 30 minutes at 0° C., a solution of 1.95 g (5.792 mmol) of the product from Example 1A in 10 ml of N,N-dimethylformamide is added dropwise, and the reaction mixture is stirred at 0° C. for a further hour. The mixture is then allowed to warm to room temperature, stirred for a further hour and then warmed to 60° C. The reaction mixture is stirred at this temperature for 15 hours. The mixture is then allowed to cool to room temperature, 80 ml of saturated sodium bicarbonate solution are added and the mixture is extracted with ethyl acetate. The organic extract is washed successively with water and saturated sodium chloride solution. The mixture is dried over anhydrous sodium sulphate, and the solvent is then removed on a rotary evaporator. The residue obtained is triturated with diisopropyl ether. The solid is filtered off with suction, washed with diisopropyl ether and dried under high vacuum. This gives 1.34 g (62% of theory) of the title compound.

$^1$H-NMR (400 MHz, DMSO-$d_6$, δ/ppm): 9.98 (s, 1H), 9.36 (s, 1H), 7.95-7.90 (m, 4H), 7.82 (d, 2H), 7.53-7.48 (m, 3H).

HPLC (Method 4): $R_t$=3.08 min.

MS (ESIpos, m/z): 375 (M+H)$^+$.

Example 3A 1-(2,4-Dimethoxyphenyl)-N-{[1-(4-iodophenyl)-3-phenyl-1H-pyrazol-4-yl]methyl}methanamine

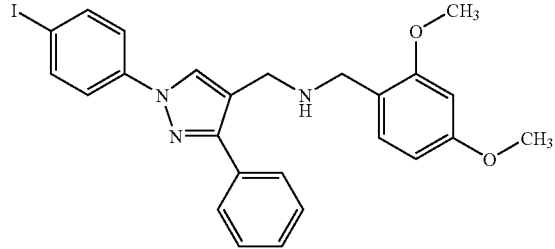

1.34 g (3.581 mmol) of the product from Example 2A and 538 µl (3.581 mmol) of 2,4-dimethoxybenzylamine are dissolved in 40 ml of dichloroethane, and the mixture is stirred at room temperature for one hour. 1.52 g (7.162 mmol) of sodium triacetoxyborohydride and 820 µl (14.33 mmol) of glacial acetic acid are then added. The reaction mixture is stirred at room temperature for 15 hours. A saturated sodium bicarbonate solution is then added, and the product is extracted with dichloromethane. The organic extract is washed with water and dried over anhydrous sodium sulphate. After filtration, the solvent is removed on a rotary evaporator. The crude product is dried under high vacuum and used without further purification in the next reaction. What is obtained are 1.89 g of the title compound.

HPLC (Method 5): $R_t$=2.10 min (60%).

MS (ESIpos, m/z): 526 (M+H)$^+$.

Example 4A

5-Chloro-N-(2,4-dimethoxybenzyl)-N-{[1-(4-iodophenyl)-3-phenyl-1H-pyrazol-4-yl]methyl}-thiophene-2-carboxamide

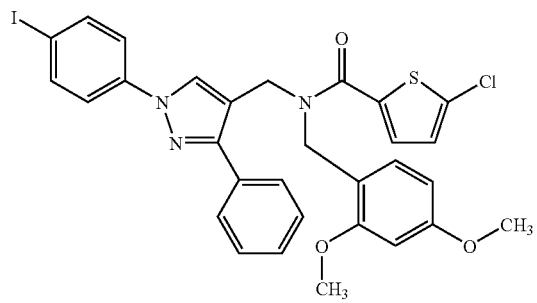

A solution of 651 mg (3.597 mmol) of 5-chlorothiophene-2-carbonyl chloride in 10 ml of anhydrous tetrahydrofuran is added to a solution of 1.89 g (3.597 mmol) of the product from Example 3A and 1.25 ml of diisopropylethylamine (Hünig-Base) in 40 ml of anhydrous tetrahydrofuran. The reaction mixture is stirred at room temperature for 15 hours. The solvent is then removed on a rotary evaporator, and the residue is taken up in dichloromethane and washed successively with saturated sodium bicarbonate solution and water. After drying over anhydrous sodium sulphate, the mixture is filtered, evaporated and the residue is purified by preparative HPLC (Method 7). This gives 1.05 g (43% of theory) of the title compound.

$^1$H-NMR (500 MHz, DMSO-$d_6$, δ/ppm): 8.53 (broad, 1H), 7.85 (d, 2H), 7.76 (d, 2H), 7.61 (d, 2H), 7.43-7.38 (m, 3H), 7.15 (broad, 1H), 7.08 (d, 1H), 7.01 (broad, 1H), 6.48-6.43 (m, 2H), 4.70 (broad, 2H), 4.58 (s, broad, 2H), 3.71 (s, 3H), 3.57 (broad, 3H).

HPLC (Method 2): $R_t$=6.47 min.

MS (ESIpos, m/z): 670/672 ($^{35}$Cl/$^{37}$Cl) (M+H)$^+$.

Example 5A

5-Chloro-N-(2,4-dimethoxybenzyl)-N-({1-[4-(3-oxomorpholin-4-yl)phenyl]-3-phenyl-1H-pyrazol-4-yl}methyl)thiophene-2-carboxamide

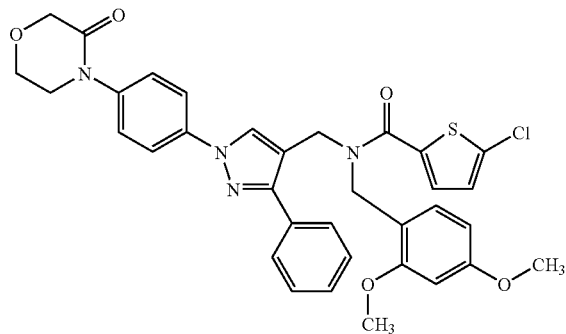

136 mg (0.203 mmol) of the product from Example 4A are dissolved in 10 ml of anhydrous dioxane, and 20.5 mg (0.203 mmol) of morpholinone, 8 mg (0.041 mmol) of copper (I) iodide, 86 mg (0.406 mmol) of potassium phosphate and 6.5 µl (0.061 mmol) of N,N'-dimethylethylenediamine are added successively. The reflux apparatus is inertized by repeatedly applying a slight vacuum and venting with argon. The reaction mixture is heated at reflux for 2 days. After this time, the mixture is allowed to cool to RT. Water is added, and the mixture is extracted with ethyl acetate. The organic extract is washed successively with water and saturated sodium chloride solution. The mixture is dried over anhydrous magnesium sulphate and filtered, and the filtrate is freed from the solvent under reduced pressure. The residue is purified by preparative HPLC (Method 7). 67 mg of the starting material are recovered, and 40 mg (60% of theory, based on 51% conversion) of the title compound are obtained.

$^1$H-NMR (400 MHz, DMSO-d$_6$, δ/ppm): 8.53 (s, broad, 1H), 7.97 (d, 2H), 7.62 (d, 2H), 7.56 (d, 2H), 7.44-7.37 (m, 3H), 7.17 (broad, 1H), 7.10 (d, 1H), 7.02 (broad, 1H), 6.50-6.44 (m, 2H), 4.73 (broad, 2H), 4.59 (broad, 2H), 4.23 (s, 2H), 4.01 (t, 2H), 3.80 (t, 2H), 3.72 (s, 3H), 3.57 (s, broad, 3H).

HPLC (Method 3): R$_t$=2.69 min.

MS (ESIpos, m/z): 643/645 ($^{35}$Cl/$^{37}$Cl) (M+H)$^+$.

Example 6A

4-Iodo-3-methylphenylhydrazine

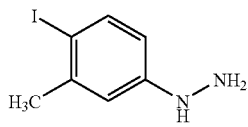

At −10° C., a solution of 345 mg (5.0 mmol) of sodium nitrite in 5 ml of water is added dropwise to a suspension of 1.165 g (5.0 mmol) of 4-iodo-3-methylaniline in 5 ml of concentrated hydrochloric acid. The mixture is stirred at about −5° C. for 45 minutes, and a solution of 5.416 g (24.0 mmol) of tin(II) chloride dihydrate in 4.5 ml of concentrated hydrochloric acid is then added dropwise at the same temperature. The mixture is then stirred at 0° C. for 10 minutes. By addition of solid sodium hydroxide, the reaction mixture is then adjusted to pH of about 14. The precipitate formed is filtered off. The filtrate is extracted with dichloromethane. The extract is washed with water, dried over anhydrous sodium sulphate, filtered and concentrated. The crude product is obtained by purification on silica gel using dichloromethane/methanol 40: as mobile phase. This gives 555 mg (38% of theory, based on a purity of 85%) of the title compound.

$^1$H-NMR (400 MHz, DMSO-d$_6$, δ/ppm): 7.42 (d, 1H), 6.79 (broad, 1H), 6.77 (d, 1H), 6.39 (dd, 1H), 3.93 (broad, 2H), 2.23 (s, 3H).

HPLC (Method 1): R$_t$=3.53 min.

MS (EI, m/z): 248 (M)$^+$.

Example 7A

Acetophenone-(4-iodo-3-methylphenyl)hydrazone

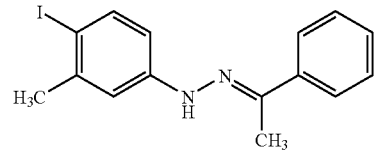

Analogously to the process described under Example 1A, 992 mg (4.0 mmol) of the compound from Example 6A and 721 mg (6.0 mmol) of acetophenone give 1.405 g (100% of theory) of the title compound.

MS (DCI, NH$_3$, m/z): 351 (M+H)$^+$.

Example 8A 1-(4-Iodo-3-methylphenyl)-3-phenyl-1H-pyrazole-4-carbaldehyde

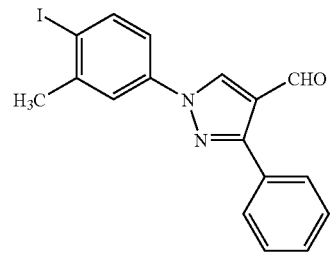

Analogously to the process described under Example 2A, 700 mg (1.999 mmol) of the compound from Example 7A give 695 mg of the title compound (59% of theory, based on a purity of 66%).

$^1$H-NMR (400 MHz, DMSO-d$_6$, δ/ppm): 9.98 (s, 1H), 9.35 (s, 1H), 8.03 (d, 1H), 8.01 (d, 1H), 7.93-7.91 (m, 2H), 7.61 (dd, 1H), 7.53-7.50 (m, 3H), 2.47 (s, 3H).

HPLC (Method 5): R$_t$=3.15 min.

MS (ESIpos, m/z): 389 (M+H)$^+$.

Example 9A 1-(2,4-Dimethoxyphenyl)-N-{[1-(4-iodo-3-methylphenyl)-3-phenyl-1H-pyrazol-4-yl]methyl}methanamine

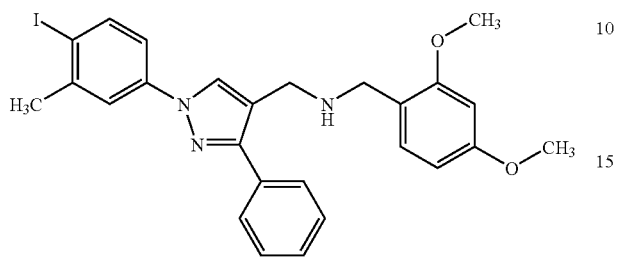

Analogously to the process described in Example 3A, 680 mg (1.752 mmol) of the compound from Example 8A give 288 mg of the title compound (27% of theory, based on a purity of 90%).

$^1$H-NMR (400 MHz, DMSO-d$_6$, δ/ppm): 8.49 (s, 1H), 7.92 (d, 1H), 7.92 (broad, 1H), 7.83 (d, 2H), 7.49 (dd, 1H), 7.43 (dd, 2H), 7.37 (dd, 1H), 7.22 (d, 1H), 6.53 (d, 1H), 6.47 (dd, 1H), 3.75 (s, 3H), 3.74 (s, 3H), 3.72-3.70 (m, 4H), 2.54 (s, 3H).

HPLC (Method 2): R$_t$=5.00 min.

MS (ESIpos, m/z): 540 (M+H)$^+$.

Example 10A

5-Chloro-N-(2,4-dimethoxybenzyl)-N-{[1-(4-iodo-3-methylphenyl)-3-phenyl-1H-pyrazol-4-yl]methyl}thiophene-2-carboxamide

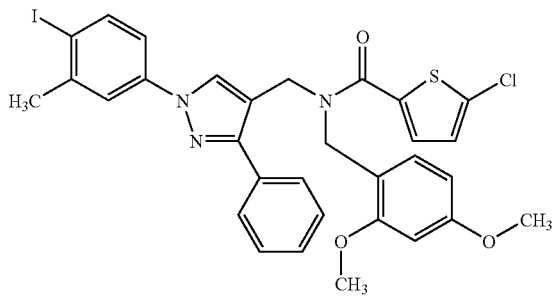

Analogously to the process described in Example 4A, 284 mg (0.526 mmol) of the compound from Example 9A give 315 mg (84% of theory) of the title compound.

$^1$H-NMR (400 MHz, DMSO-d$_6$, δ/ppm): 8.50 (broad, 1H), 7.93-7.91 (m, 2H), 7.61 (d, 2H), 7.53 (dd, 1H), 7.44-7.38 (m, 3H), 7.17 (broad, 1H), 7.08 (d, 1H), 7.02 (broad, 1H), 6.48 (broad, 1H), 6.45 (dd, 1H), 4.72 (broad, 2H), 4.58 (broad, 2H), 3.71 (s, 3H), 3.56 (broad, 3H), 2.47 (s, 3H).

HPLC (Method 2): R$_t$=6.52 min.

MS (ESIpos, m/z): 684/686 ($^{35}$Cl/$^{37}$Cl) (M+H)$^+$.

Example 11A

5-Chloro-N-(2,4-dimethoxybenzyl)-N-({1-[3-methyl-4-(3-oxomorpholin-4-yl)phenyl]-3-phenyl-1H-pyrazol-4-yl}methyl)thiophene-2-carboxamide

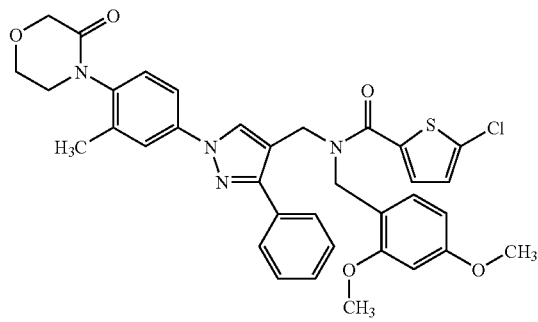

Analogously to the process described in Example 5A, 150 mg (0.219 mmol) of the compound from Example 10A and 33.3 mg (0.329 mmol) of morpholinone give 93 mg (64% of theory) of the title compound.

$^1$H-NMR (400 MHz, DMSO-d$_6$, δ/ppm): 8.48 (broad, 1H), 7.87 (d, 1H), 7.80 (dd, 2H), 7.61 (d, 2H), 7.45-7.37 (m, 4H), 7.16 (broad, 1H), 7.08 (d, 1H), 7.02 (broad, 1H), 6.48 (broad, 1H), 6.44 (dd, 1H), 4.72 (broad, 2H), 4.59 (broad, 2H), 4.27-4.18 (m, 2H), 4.03-3.98 (m, 2H), 3.71 (s, 3H), 3.59-3.47 (m, 2H), 3.56 (s, 3H), 2.23 (s, 3H).

HPLC (Method 1): R$_t$=5.15 min.

MS (ESIpos, m/z): 657/659 ($^{35}$Cl/$^{37}$Cl) (M+H)$^+$.

Example 12A

Methyl 3-pyridyl ketone (4-iodophenyl)hydrazone

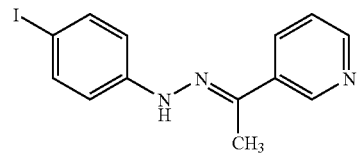

Analogously to the process described in Example 1A, 5.0 g (21.36 mmol) of 4-iodophenylhydrazine and 3-acetylpyridine give 5.15 g (71% of theory) of the title compound.

$^1$H-NMR (500 MHz, DMSO-d$_6$, δ/ppm): 9.61 (s, 1H), 8.97 (s, 1H), 8.48 (d, 1H), 8.12 (d, 1H), 7.52 (d, 2H), 7.40 (dd, 1H), 7.11 (d, 2H), 2.28 (s, 3H).

HPLC (Method 1): R$_t$=4.09 min.

MS (DCI, NH$_3$, m/z): 338 (M+H)$^+$.

Example 13A 1-(4-Iodophenyl)-3-pyridin-3-yl-1H-pyrazole-4-carbaldehyde

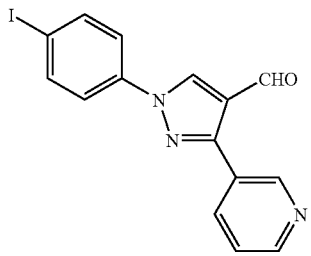

Analogously to the process described in Example 2A, 5.1 g (15.12 mmol) of the compound from Example 12A give 4.33 g (76% of theory) of the title compound.

$^1$H-NMR (400 MHz, DMSO-d$_6$, δ/ppm): 9.99 (s, 1H), 9.43 (s, 1H), 9.10 (d, 1H), 8.68 (dd, 1H), 8.32 (d, 1H), 7.95 (d, 2H), 7.83 (d, 2H), 7.56 (dd, 1H).

HPLC (Method 1): R$_t$=3.99 min.
MS (DCI, NH$_3$, m/z): 376 (M+H)$^+$, 393 (M+NH$_4$)$^+$.

Example 14A 1-(2,4-Dimethoxyphenyl)-N-{[1-(4-iodophenyl)-3-pyridin-3-yl-1H-pyrazol-4-yl]methyl}-methanamine

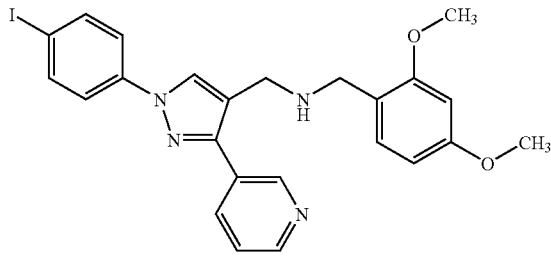

Analogously to the process described in Example 3A, 4.33 g (11.54 mmol) of the compound from Example 13A give 6.07 g (99% of theory) of the title compound, which is used without further purification in the next synthesis step.

HPLC (Method 5): R$_t$=1.75 min (60%).
MS (ESIpos, m/z): 527 (M+H)$^+$.

Example 15A

5-Chloro-N-(2,4-dimethoxybenzyl)-N-{[1-(4-iodophenyl)-3-pyridin-3-yl-1H-pyrazol-4-yl]methyl}-thiophene-2-carboxamide

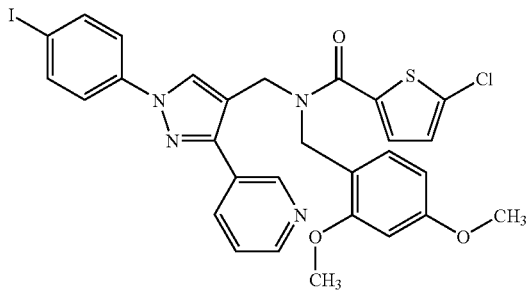

Analogously to the process described under Example 4A, 6.07 g (11.54 mmol) of the compound from Example 14A are converted into 2.57 g (33% of theory) of the title compound.

$^1$H-NMR (400 MHz, DMSO-d$_6$, δ/ppm): 8.81 (d, 1H), 8.58-8.53 (m, 2H), 7.98 (dd, 1H), 7.87 (d, 2H), 7.77 (d, 2H), 7.43 (dd, 1H), 7.17 (broad, 1H), 7.09 (d, 1H), 7.00 (broad, 1H), 6.46 (broad, 1H), 6.42 (dd, 1H), 4.70 (broad, 2H), 4.58 (broad, 2H), 3.71 (s, 3H), 3.57 (broad, 3H).

HPLC (Method 2): R$_t$=4.95 min.
MS (ESIpos, m/z): 671/673 ($^{35}$Cl/$^{37}$Cl) (M+H)$^+$.

Example 16A

5-Chloro-N-(2,4-dimethoxybenzyl)-N-({1-[4-(3-oxomorpholin-4-yl)phenyl]-3-pyridin-3-yl-1H-pyrazol-4-yl}methyl)thiophene-2-carboxamide

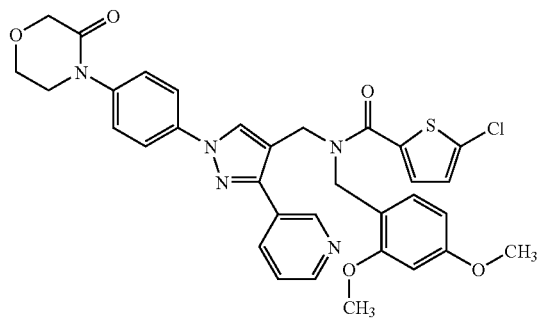

Analogously to the process described under Example 5A, 145 mg (0.216 mmol) of the compound from Example 15A are converted into 117 mg (81% of theory) of the title compound.

$^1$H-NMR (400 MHz, DMSO-d$_6$, δ/ppm): 8.81 (d, 1H), 8.57 (dd, 1H), 8.53 (broad, 1H), 7.99 (dd, 1H), 7.95 (d, 2H), 7.57 (d, 2H), 7.45 (dd, 1H), 7.17 (broad, 1H), 7.08 (d, 1H), 6.99 (broad, 1H), 6.47 (broad, 1H), 6.43 (dd, 1H), 4.72 (broad, 2H), 4.59 (broad, 2H), 4.23 (s, 2H), 4.01 (t, 2H), 3.79 (t, 2H), 3.72 (s, 3H), 3.58 (s, broad, 3H).

HPLC (Method 2): R$_t$=4.26 min.
MS (ESIpos, m/z): 644/646 ($^{35}$Cl/$^{37}$Cl) (M+H)$^+$.

Example 17A

5-Chloro-N-(2,4-dimethoxybenzyl)-N-({1-[4-(2-oxopiperidin-1-yl)phenyl]-3-pyridin-3-yl-1H-pyrazol-4-yl}methyl)thiophene-2-carboxamide

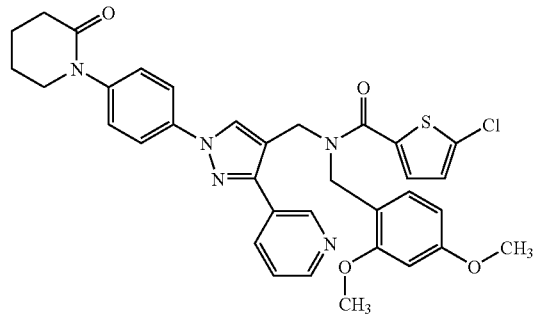

Analogously to the process described under Example 5A, 177 mg (0.264 mmol) of the compound from Example 15A and piperidin-2-one are converted into 70 mg (40% of theory) of the title compound.

¹H-NMR (500 MHz, DMSO-d₆, δ/ppm): 8.83 (broad, 1H), 8.58 (broad, 1H), 8.53 (broad, 1H), 8.00 (d, 1H), 7.92 (d, 2H), 7.47-7.41 (m, 3H), 7.17 (broad, 1H), 7.08 (d, 1H), 6.99 (broad, 1H), 6.47 (broad, 1H), 6.43 (dd, 1H), 4.72 (broad, 2H), 4.59 (broad, 2H), 3.71 (s, 3H), 3.64 (t, 2H), 3.57 (s, broad, 3H), 2.42 (t, 2H), 1.91-1.83 (m, 4H).

HPLC (Method 2): $R_t$=4.34 min.

MS (DCI, NH₃, m/z): 642/644 ($^{35}$Cl/$^{37}$Cl) (M+H)⁺.

Example 18A

Methyl 4-pyridyl ketone (4-iodophenyl)hydrazone

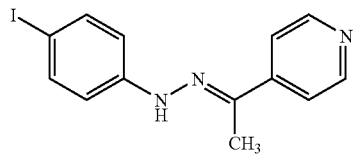

Analogously to the process described in Example 1A, 5.0 g (21.36 mmol) of 4-iodophenylhydrazine and 4-acetylpyridine give 6.67 g (92% of theory) of the title compound.

¹H-NMR (500 MHz, DMSO-d₆, δ/ppm): 9.78 (s, 1H), 8.54 (d, 2H), 7.70 (d, 2H), 7.54 (d, 2H), 7.14 (d, 2H), 2.23 (s, 3H).

HPLC (Method 1): $R_t$=4.11 min.

MS (DCI, NH₃, m/z): 338 (M+H)⁺.

Example 19A 1-(4-Iodophenyl)-3-pyridin-4-yl-1H-pyrazole-4-carbaldehyde

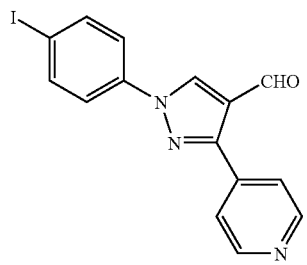

Analogously to the process described in Example 2A, 3.0 g (8.90 mmol) of the compound from Example 18A give 468 mg (14% of theory) of the title compound.

HPLC (Method 6): $R_t$=2.02 min.

MS (ESIpos, m/z): 376 (M+H)⁺.

Example 20A 1-(2,4-Dimethoxyphenyl)-N-{[1-(4-iodophenyl)-3-pyridin-4-yl-1H-pyrazol-4-yl]methyl}-methanamine

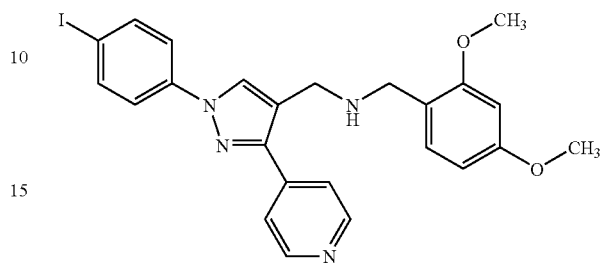

Analogously to the process described under Example 3A, 468 mg (1.249 mmol) of the compound from Example 19A give 657 mg (99% of theory) of the title compound, which is used without further purification in the next synthesis step.

HPLC (Method 3): $R_t$=1.49 min (77%).

MS (ESIpos, m/z): 527 (M+H)⁺.

Example 21A

5-Chloro-N-(2,4-dimethoxybenzyl)-N-{[1-(4-iodophenyl)-3-pyridin-4-yl-1H-pyrazol-4-yl]methyl}-thiophene-2-carboxamide

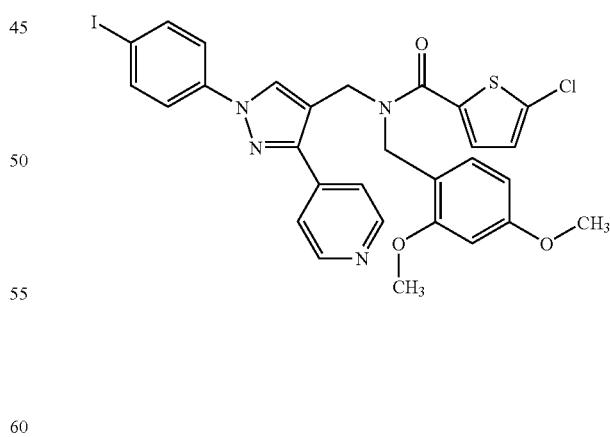

Analogously to the process described under Example 4A, 657 mg (1.249 mmol) of the compound from Example 20A are converted into 405 mg (48% of theory) of the title compound.

HPLC (Method 5): $R_t$=2.96 min (99%).

MS (ESIpos, m/z): 671/673 ($^{35}$Cl/$^{37}$Cl) (M+H)⁺.

Example 22A

5-Chloro-N-(2,4-dimethoxybenzyl)-N-({1-[4-(3-oxomorpholin-4-yl)phenyl]-3-pyridin-4-yl-1H-pyrazol-4-yl}methyl)thiophene-2-carboxamide

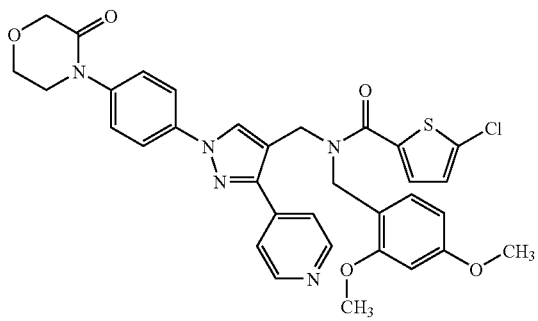

Analogously to the process described under Example 5A, 150 mg (0.224 mmol) of the compound from Example 21A are converted into 120 mg (84% of theory) of the title compound.

$^1$H-NMR (400 MHz, DMSO-d$_6$, δ/ppm): 8.61 (d, 2H), 8.59 (broad, 1H), 7.98 (d, 2H), 7.64 (d, 2H), 7.57 (2H, d), 7.18 (broad, 1H), 7.09 (d, 1H), 7.03 (broad, 1H), 6.48 (broad, 1H), 6.45 (dd, 1H), 4.78 (broad, 2H), 4.62 (broad, 2H), 4.23 (s, 2H), 4.00 (t, 2H), 3.79 (t, 2H), 3.72 (s, 3H), 3.57 (s, broad, 3H).

HPLC (Method 2): R$_t$=4.20 min.

MS (DCI, NH$_3$, m/z): 644/646 ($^{35}$Cl/$^{37}$Cl) (M+H)$^+$.

Example 23A

5-Chloro-N-(2,4-dimethoxybenzyl)-N-({1-[4-(2-oxopiperidin-1-yl)phenyl]-3-pyridin-4-yl-1H-pyrazol-4-yl}methyl)thiophene-2-carboxamide

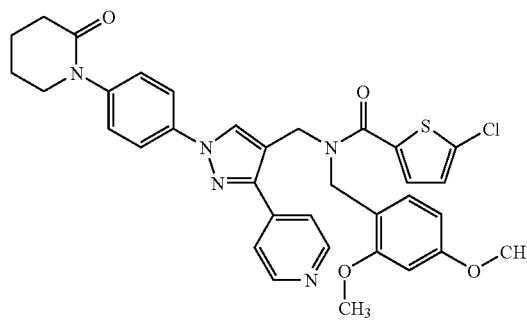

Analogously to the process described under Example 5A, 248 mg (0.371 mmol) of the compound from Example 21A and piperidin-2-one are converted into 66 mg (28% of theory) of the title compound.

$^1$H-NMR (500 MHz, DMSO-d$_6$, δ/ppm): 8.61-8.53 (m, 2H), 8.13 (s, 1H), 7.93 (d, 2H), 7.62 (d, 2H), 7.43 (d, 2H), 7.18 (broad, 1H), 7.09 (d, 1H), 7.03 (broad, 1H), 6.47 (broad, 1H), 6.45 (dd, 1H), 4.78 (broad, 2H), 4.61 (broad, 2H), 3.71 (s, 3H), 3.65 (t, 2H), 3.57 (s, broad, 3H), 2.41 (t, 2H), 1.91-1.82 (m, 4H).

HPLC (Method 2): R$_t$=4.38 min.

MS (ESIpos, m/z): 642/644 ($^{35}$Cl/$^{37}$Cl) (M+H)$^+$.

WORKING EXAMPLES

Example 1

5-Chloro-N-({1-[4-(3-oxomorpholin-4-yl)phenyl]-3-phenyl-1H-pyrazol-4-yl}methyl)thiophene-2-carboxamide

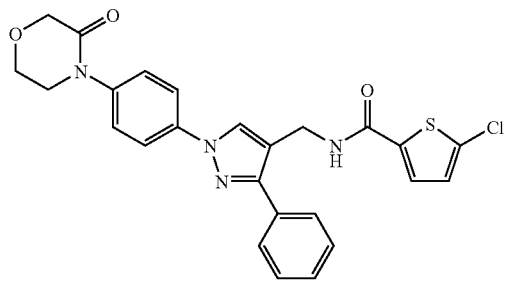

0.5 ml of trifluoroacetic acid is added to a solution of 39 mg (0.061 mmol) of the compound from Example 5A in 5 ml of dichloromethane, and the mixture is stirred at room temperature for 30 minutes. The reaction mixture is then evaporated to dryness, and the residue is taken up in acetonitrile. Insoluble material is filtered off, and the filtrate is, after concentration, purified by preparative HPLC (Method 7). This gives 26 mg (85% of theory) of the title compound.

$^1$H-NMR (400 MHz, DMSO-d$_6$, δ/ppm): 9.05 (t, 1H), 8.54 (s, 1H), 7.93 (d, 2H), 7.71 (d, 2H), 7.70 (d, 1H), 7.55 (d, 2H), 7.48 (dd, 2H), 7.41 (dd, 1H), 7.19 (d, 1H), 4.53 (d, 2H), 4.00 (t, 2H), 3.78 (t, 2H).

HPLC (Method 2): R$_t$=4.57 min.

MS (ESIpos, m/z): 493/495 ($^{35}$Cl/$^{37}$Cl) (M+H)$^+$.

Example 2

5-Chloro-N-({1-[3-methyl-4-(3-oxomorpholin-4-yl)phenyl]-3-phenyl-1H-pyrazol-4-yl}methyl)-thiophene-2-carboxamide

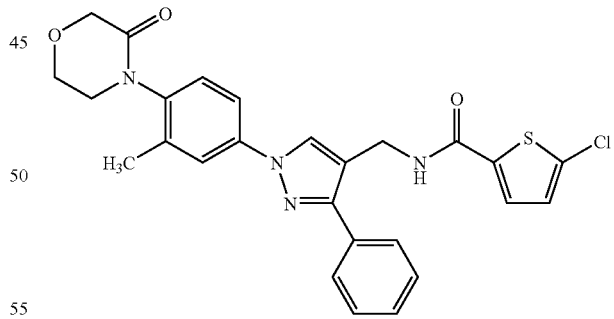

Analogously to the process described under Example 1, 88 mg (0.134 mmol) of the compound from Example 11A give 58 mg (86% of theory) of the title compound.

$^1$H-NMR (400 MHz, DMSO-d$_6$, δ/ppm): 9.01 (t, broad, 1H), 8.52 (s, 1H), 7.84 (d, 1H), 7.79-7.73 (m, 3H), 7.69 (d, 1H), 7.50-7.46 (m, 2H), 7.42-7.37 (m, 2H), 7.18 (d, 1H), 4.53 (d, 2H), 4.28-4.17 (m, 2H), 4.02-3.97 (m, 2H), 3.77-3.68 (m, 2H), 2.22 (s, 3H).

HPLC (Method 2): R$_t$=4.59 min.

MS (ESIpos, m/z): 507/509 ($^{35}$Cl/$^{37}$Cl) (M+H)$^+$.

Example 3

5-Chloro-N-({1-[4-(3-oxomorpholin-4-yl)phenyl]-3-pyridin-3-yl-1H-pyrazol-4-yl}methyl)thiophene-2-carboxamide hydrochloride

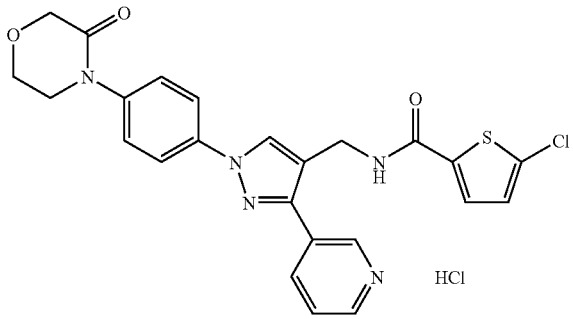

Analogously to the process described under Example 1, 115 mg (0.179 mmol) of the compound from Example 16A give 71 mg (75% of theory) of the title compound which, by dissolution in methanol and 1 molar hydrochloric acid and subsequent concentration, is converted into the hydrochloride salt.

$^1$H-NMR (400 MHz, DMSO-$d_6$, δ/ppm): 9.07-9.03 (m, 2H), 8.71 (d, 1H), 8.63 (s, 1H), 8.38 (d, 1H), 7.96 (d, 2H), 7.70 (dd, 1H), 7.67 (d, 1H), 7.58 (d, 2H), 7.17 (d, 1H), 4.58 (d, 2H), 4.23 (s, 2H), 4.00 (t, 2H), 3.78 (t, 2H).

HPLC (Method 2): $R_t$=3.76 min.

MS (ESIpos, m/z): 494/496 ($^{35}$Cl/$^{37}$Cl) (M+H)$^+$.

Example 4

5-Chloro-N-({1-[4-(2-oxopiperidin-1-yl)phenyl]-3-pyridin-3-yl-1H-pyrazol-4-yl}methyl)thiophene-2-carboxamide hydrochloride

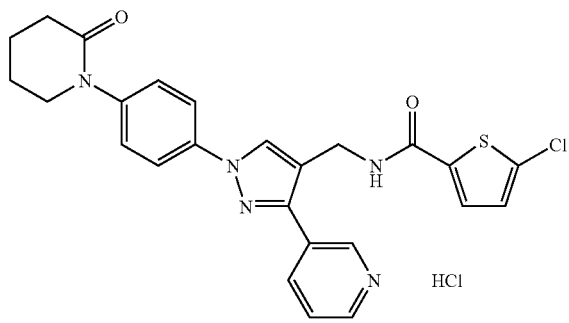

Analogously to the process described under Example 1, 68 mg (0.107 mmol) of the compound from Example 17A give 44 mg (79% of theory) of the title compound, which, by dissolution in methanol and 1 molar hydrochloric acid and subsequent concentration, is converted into the hydrochloride salt.

$^1$H-NMR (500 MHz, DMSO-$d_6$, δ/ppm): 9.10 (s, 1H), 9.09 (t, 1H), 8.74 (dd, 1H), 8.63 (s, 1H), 8.48 (dd, 1H), 7.91 (d, 2H), 7.81-7.77 (m, 1H), 7.66 (d, 1H), 7.45 (d, 2H), 7.18 (d, 1H), 4.58 (d, 2H), 3.64 (t, 2H), 2.42 (t, 2H), 1.91-1.82 (m, 4H).

HPLC (Method 2): $R_t$=3.86 min.

MS (DCI, NH$_3$, m/z): 492/494 ($^{35}$Cl/$^{37}$Cl) (M+H)$^+$.

Example 5

5-Chloro-N-({1-[4-(3-oxomorpholin-4-yl)phenyl]-3-pyridin-4-yl-1H-pyrazol-4-yl}methyl)thiophene-2-carboxamide hydrochloride

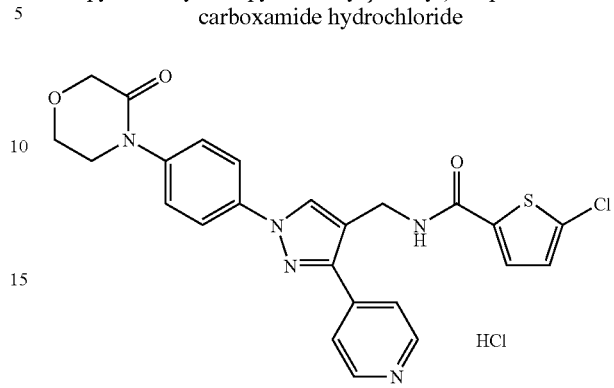

Analogously to the process described in Example 1, 108 mg (0.168 mmol) of the compound from Example 22A give 66 mg (75% of theory) of the title compound which, by dissolution with methanol and 1 molar hydrochloric acid and subsequent concentration, is converted into the hydrochloride salt.

$^1$H-NMR (500 MHz, DMSO-$d_6$, δ/ppm): 9.13 (1H), 8.85 (2H), 8.70 (1H), 8.18 (2H), 8.00 (2H), 7.68 (1H), 7.61 (2H), 7.19 (1H), 4.66 (2H), 4.23 (2H), 4.00 (2H), 3.80 (2H).

HPLC (Method 2): $R_t$=3.72 min.

MS (DCI, NH$_3$, m/z): 494/496 ($^{35}$Cl/$^{37}$Cl) (M+H)$^+$.

Example 6

5-Chloro-N-({1-[4-(2-oxopiperidin-1-yl)phenyl]-3-pyridin-4-yl-1H-pyrazol-4-yl}methyl)thiophene-2-carboxamide

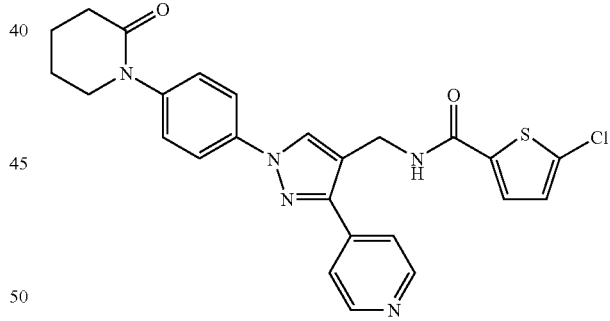

Analogously to the process described under Example 1, 65 mg (0.101 mmol) of the compound from Example 23A give 36 mg (68% of theory) of the title compound.

$^1$H-NMR (400 MHz, DMSO-$d_6$, δ/ppm): 9.10 (t, 1H), 8.81 (d, 2H), 8.64 (s, 1H), 8.10 (d, 2H), 7.94 (d, 2H), 7.67 (d, 1H), 7.47 (d, 2H), 7.18 (d, 1H), 4.64 (d, 2H), 3.65 (t, 2H), 2.42 (t, 2H), 1.93-1.82 (m, 4H).

HPLC (Method 2): $R_t$=3.82 min.

MS (ESIpos, m/z): 492/494 ($^{35}$Cl/$^{37}$Cl) (M+H)$^+$.

B. EVALUATION OF THE PHARMACOLOGICAL ACTIVITY

The compounds according to the invention act in particular as selective inhibitors of blood coagulation factor Xa and do not, or only at significantly higher concentrations, inhibit other serine proteases, such as plasmin or trypsin.

"Selective" are those inhibitors of the blood coagulation factor Xa in which the IC$_{50}$ values for the factor Xa inhibition are lower by a factor of at least 100 compared to the IC$_{50}$ values for the inhibition of other serine proteases, in particular plasmin and trypsin, where, with respect to the test methods for the selectivity, reference is made to the test methods, described below, of Examples B.a.1) and B.a.2).

The advantageous pharmacological properties of the compounds according to the invention can be determined by the following methods:

a) Test Descriptions (In Vitro)

a.1) Determination of the Factor Xa Inhibition

In order to determine the factor Xa inhibition of the substances listed above, a biochemical test system is set up, in which the conversion of a factor Xa substrate is used to determine the enzymatic activity of human factor Xa. Here Factor Xa cleaves aminomethylcoumarin, whose fluorescence is measured, from the peptidic substrate. The determinations are carried out in microtitre plates.

Substances to be tested, in various concentrations, are dissolved in dimethyl sulphoxide and incubated for 15 min at 22° C. with human factor Xa (1.3 nmol/l dissolved in 50 mmol/l of Tris buffer [C,C,C-tris(hydroxymethyl)aminomethane], 100 mmol/l NaCl, 0.1% BSA [bovine serum albumin], pH 7.4). The substrate (5 μmol/l of Boc-Ile-Glu-Gly-Arg-AMC from Bachem) is then added. After an incubation time of 30 min, the sample is excited at a wavelength of 360 nm, and the emission at 460 nm is measured. The measured emissions of the test batches with test substance are compared to the control batches without test substance (only dimethyl sulphoxide instead of test substance in dimethyl sulphoxide), and IC$_{50}$ values are calculated from the concentration/activity relationships.

Representative activity data from this test are listed in Table 1 below:

TABLE 1

| Example No. | IC$_{50}$ [nM] |
|---|---|
| 1 | 0.7 |
| 2 | 0.7 |
| 3 | 0.8 | a.2) Determination of the Selectivity

To demonstrate the selectivity of the substances with respect to factor Xa inhibition, the test substances are examined for their inhibition of other human serine proteases, such as trypsin and plasmin. To determine the enzymatic activity of trypsin (83 mU/ml from Sigma) and plasmin (0.1 μg/ml from Kordia), these enzymes are dissolved (50 mmol/l of Tris buffer [C,C,C-tris(hydroxymethyl)aminomethane], 100 mmol/l of NaCl, 0.1% BSA [bovine serum albumin], 5 mmol/l of calcium chloride, pH 7.4) and incubated for 15 min with various concentrations of test substance in dimethyl sulphoxide and also with dimethyl sulphoxide without test substance. The enzymatic reaction is then started by addition of the appropriate substrates (5 μmol/l of Boc-Ile-Glu-Gly-Arg-AMC from Bachem for trypsin, 50 μmol/l of MeOSuc-Ala-Phe-Lys-AMC from Bachem for plasmin). After an incubation time of 30 min at 22° C., the fluorescence is measured (excitation: 360 nm, emission: 460 nm). The measured emissions of the test batches with test substance are compared to the control batches without test substance (only dimethyl sulphoxide instead of test substance in dimethyl sulphoxide), and IC$_{50}$ values are calculated from the concentration/activity relationships.

a.3) Determination of the Anticoagulatory Activity:

The anticoagulatory activity of the test substances is determined in vitro in human and rabbit plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 2500 g for 10 minutes. The supernatant is pipetted off. The prothrombin time (PT, synonyms: thromboplastin time, quick test) is determined in the presence of varying concentrations of test substance or the corresponding solvent using a commercial test kit (Hemoliance® RecombiPlastin, from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

b) Determination of the Antithrombotic Activity (In Vivo)

b.1) Arteriovenos Shunt Model (Rabbit):

Fasting rabbits (strain: Esd: NZW) are anaesthetized by intramuscular administration of Rompun/Ketavet solution (5 mg/kg and 40 mg/kg, respectively). Thrombus formation is initiated in an arteriovenous shunt in accordance with the method described by C. N. Berry et al. [Semin. Thromb. Hemost. 1996, 22, 233-241]. To this end, the left jugular vein and the right carotid artery are exposed. The two vessels are connected by an extracorporeal shunt using a vein catheter of a length of 10 cm. In the middle, this catheter is attached to a further polyethylene tube (PE 160, Becton Dickenson) of a length of 4 cm which contains a roughened nylon thread which has been arranged to form a loop, to form a thrombogenic surface. The extracorporeal circulation is maintained for 15 minutes. The shunt is then removed and the nylon thread with the thrombus is weighed immediately. The weight of the nylon thread on its own was determined before the experiment was started. Before extracorporeal circulation is set up, the test substances are administered either intravenously via an ear vein or orally using a pharyngeal tube.

C. EXEMPLARY EMBODIMENTS OF PHARMACEUTICAL COMPOSITIONS

The compounds according to the invention can be converted into pharmaceutical preparations in the following ways:

Tablet:

Composition:

100 mg of the compound according to the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Preparation:

The mixture of the compound according to the invention, lactose and starch is granulated with a 5% strength solution (m/m) of PVP in water. The granules are dried and then mixed with the magnesium stearate for 5 minutes. This mixture is compressed using a conventional tablet press (see above for format of the tablet). As guideline, a compressive force of 15 kN is used for the compression.

Oral Suspension:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension are equivalent to a single dose of 100 mg of the compound according to the invention.
Preparation:
The Rhodigel is suspended in ethanol, and the compound according to the invention is added to the suspension. The water is added while stirring. The mixture is stirred for about 6 h until the swelling of the Rhodigel is complete.
Oral Solution:
Composition:
500 mg of the compound according to the invention, 2.5 g of polysorbate and 97 g of polyethylene glycol 400. 20 g of oral solution are equivalent to a single dose of 100 mg of the compound according to the invention.
Production:
The compound according to the invention is suspended in the mixture of polyethylene glycol and polysorbate while stirring. Stirring is continued until the compound according to the invention is completely dissolved.
i.v. Solution:
The compound according to the invention is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

The invention claimed is:

1. A compound of the formula (I)

in which

E represents a group of the formula where $R^1$ represents hydrogen, hydroxy, amino, $C_1$-$C_4$-alkyl, $C_1$-$C_4$-alkoxy, $C_1$-$C_4$-alkylamino, $C_3$-$C_6$-cycloalkyl, $C_3$-$C_6$-cycloalkyloxy, $C_3$-$C_6$-cycloalkylamino, $C_1$-$C_4$-alkylcarbonylamino or $C_1$-$C_4$-alkoxycarbonylamino, where alkyl, alkoxy, alkylamino may be substituted by a substituent, the substituent being selected from the group consisting of hydroxy, amino, $C_1$-$C_4$-alkoxy, $C_1$-$C_4$-alkylamino, $C_3$-$C_6$-cycloalkylamino and a 4- to 7-membered saturated heterocyclyl bound via an N atom which may contain a ring member from the group consisting of N—$R^5$ or O, where $R^5$ represents hydrogen or $C_1$-$C_4$-alkyl, and $R^{10}$ represents hydrogen, $C_1$-$C_4$-alkyl, $C_1$-$C_4$-alkoxy, $C_3$-$C_6$-cycloalkyl, $C_3$-$C_6$-cycloalkyloxy or —$NR^{11}R^{12}$, where $R^{11}$ represents $C_1$-$C_4$-alkyl or $C_3$-$C_6$-cycloalkyl, and $R^{12}$ represents $C_1$-$C_4$-alkyl, A represents a 5-membered heteroaryl or partially unsaturated 5-membered heterocyclyl, where heteroaryl and heterocyclyl are attached in the 1- or 2-position to the phenyl ring and heteroaryl and heterocyclyl for their part have a 1,3-attachment to the phenyl ring and the carbonylaminomethyl group, and where heteroaryl and heterocyclyl are substituted by a substituent $R^6$, where $R^6$ is attached to the neighbouring atom of the atom to which the carbonylaminomethyl group is attached and has a 1,4-attachment to the phenyl ring and where the atom to which $R^6$ is attached is a nitrogen or carbon atom and where $R^6$ represents phenyl or a 5- or 6-membered heteroaryl, where phenyl and heteroaryl may be substituted by 1 to 3 substituents, where the substituents independently of one another are selected from the group consisting of halogen, hydroxy, hydroxymethyl, hydroxyethyl, amino, aminomethyl, aminoethyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, hydroxycarbonyl, hydroxycarbonylmethyl, aminocarbonyl, aminocarbonylmethyl, $C_1$-$C_4$-alkoxycarbonyl, $C_1$-$C_4$-alkoxycarbonylmethyl, $C_1$-$C_4$-alkylaminocarbonyl, $C_1$-$C_4$-alkylaminocarbonylmethyl, aminosulphonyl, $C_1$-$C_4$-alkylaminosulphonyl and $C_1$-$C_4$-alkylsulphonyl, $R^2$ represents hydrogen, fluorine, chlorine, cyano, hydroxy, amino, trifluoromethyl, trifluoromethoxy, $C_1$-$C_4$-alkyl, $C_1$-$C_4$-alkoxy, $C_1$-$C_4$-alkoxymethyl, $C_1$-$C_4$-alkylamino, $C_3$-$C_6$-cycloalkyl, aminocarbonyl, $C_1$-$C_4$-alkoxycarbonyl or $C_1$-$C_4$-alkylaminocarbonyl, $R^3$ represents hydrogen, fluorine, chlorine, cyano, hydroxy, amino, trifluoromethyl, trifluoromethoxy, $C_1$-$C_4$-alkyl, $C_1$-$C_4$-alkoxy, $C_1$-$C_4$-alkoxymethyl, $C_1$-$C_4$-alkylamino, $C_3$-$C_6$-cycloalkyl, aminocarbonyl, $C_1$-$C_4$-alkoxycarbonyl or $C_1$-$C_4$-alkylaminocarbonyl, $R^4$ represents a group of the formula

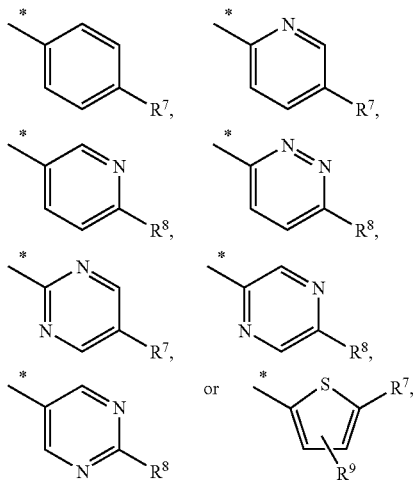

where

* is the point of attachment to the carbonyl group, $R^7$ represents hydrogen, fluorine, chlorine, cyano, ethynyl, $C_1$-$C_4$-alkyl, $C_1$-$C_4$-alkoxy or $C_3$-$C_6$-cycloalkyl, $R^8$ represents hydrogen, amino, $C_1$-$C_4$-alkyl, $C_1$-$C_4$-alkylamino or $C_3$-$C_6$-cycloalkyl, and $R^9$ represents hydrogen, fluorine, chlorine, amino or $C_1$-$C_4$-alkyl, or one of its salts, its solvates or the solvates of its salts.

2. A compound according to claim 1, wherein

E represents a group of the formula

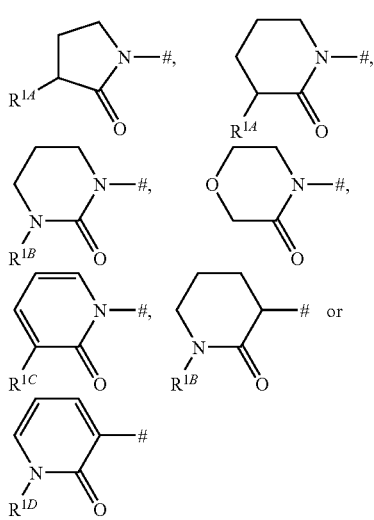

where # is the point of attachment to the phenyl ring, $R^{1A}$ represents hydrogen, hydroxy, hydroxymethyl, 2-hydroxyethyl, amino or methoxy, $R^{1B}$ represents hydrogen, hydroxy, amino, methyl or ethyl, where methyl may be substituted by a pyrrolidin-1-yl substituent, and ethyl may be substituted by a substituent, where the substituent is selected from the group consisting of hydroxy, amino, dimethylamino and cyclopropylamino, $R^{1C}$ represents hydrogen, methyl or ethyl, in which methyl may be substituted by a substituent, where the substituent is selected from the group consisting of hydroxy and pyrrolidin-1-yl, and ethyl may be substituted by a substituent, where the substituent is selected from the group consisting of hydroxy, amino and cyclopropylamino, and $R^{1D}$ represents hydrogen, methyl or ethyl, in which methyl may be substituted by a substituent, where the substituent is selected from the group consisting of cyclopropylamino and pyrrolidin-1-yl, and ethyl may be substituted by a substituent, where the substituent is selected from the group consisting of hydroxy, amino and cyclopropylamino, A represents a 5-membered heteroaryl or partially unsaturated 5-membered heterocyclyl, where heteroaryl and heterocyclyl are attached in the 1- or 2-position to the phenyl ring and heteroaryl and heterocyclyl for their part have a 1,3-attachment to the phenyl ring and the carbonylaminomethyl group, and where heteroaryl and heterocyclyl are substituted by a substituent $R^6$, where $R^6$ is attached to the neighbouring atom of the atom to which the carbonylaminomethyl group is attached and has a 1,4-attachment to the phenyl ring and where the atom to which $R^6$ is attached is a nitrogen or carbon atom and where $R^6$ represents phenyl or a 5- or 6-membered heteroaryl, where phenyl and heteroaryl may be substituted by 1 to 3 substituents, where the substituents independently of one another are selected from the group consisting of halogen, hydroxy, amino, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, hydroxycarbonyl, hydroxycarbonylmethyl, aminocarbonyl, aminocarbonylmethyl, $C_1$-$C_4$-alkoxycarbonyl, $C_1$-$C_4$-alkoxycarbonylmethyl, $C_1$-$C_4$-alkylaminocarbonyl, $C_1$-$C_4$-alkylaminocarbonylmethyl, aminosulphonyl, $C_1$-$C_4$-alkylaminosulphonyl and $C_1$-$C_4$-alkylsulphonyl, $R^2$ represents hydrogen, fluorine, chlorine, cyano, hydroxy, $C_1$-$C_4$-alkyl or $C_1$-$C_4$-alkoxy, $R^3$ represents hydrogen, fluorine, chlorine, cyano, hydroxy, $C_1$-$C_4$-alkyl, $C_1$-$C_4$-alkoxy, $C_1$-$C_4$-alkoxymethyl, cyclopropyl, aminocarbonyl, $C_1$-$C_4$-alkoxycarbonyl or $C_1$-$C_4$-alkylaminocarbonyl, R⁴ represents a group of the formula where
* is the point of attachment to the carbonyl group,
R⁷ represents fluorine, chlorine, ethynyl, methyl or methoxy,
and
R⁹ represents hydrogen.

3. A compound according to claim 1, wherein
E represents a group of the formula where
# is the point of attachment to the phenyl ring,
A represents pyrazolyl, oxadiazolyl or isoxazolinyl,
where pyrazolyl, oxadiazolyl and isoxazolinyl are attached in the 1-position to the phenyl ring and pyrazolyl, oxadiazolyl and isoxazolinyl for their part have a 1,3-attachment to the phenyl ring and the carbonylaminomethyl group,
and
where pyrazolyl, oxadiazolyl and isoxazolinyl are substituted by a substituent R⁶, where R⁶ is attached to the neighbouring atom of the atom to which the carbonylaminomethyl group is attached and has a 1,4-attachment to the phenyl ring
and
where the atom to which R⁶ is attached is a nitrogen or carbon atom
and
where
R⁶ represents phenyl, pyrid-2-yl, pyrid-3-yl, pyrid-4-yl, 1,3-oxazol-2-yl or pyrimidin-2-yl,
where phenyl, pyrid-2-yl, pyrid-3-yl, pyrid-4-yl, 1,3-oxazol-2-yl and pyrimidin-2-yl may be substituted by 1 to 3 substituents, where the substituents independently of one another are selected from the group consisting of halogen, hydroxy, amino, $C_1$-$C_4$-alkyl, $C_1$-$C_4$-alkoxy, $C_1$-$C_4$-alkylamino, hydroxycarbonyl, aminocarbonyl, $C_1$-$C_4$-alkoxycarbonyl, $C_1$-$C_4$-alkylaminocarbonyl, aminosulphonyl, $C_1$-$C_4$-alkylaminosulphonyl and $C_1$-$C_4$-alkylsulphonyl,
R² represents hydrogen or fluorine,
R³ represents hydrogen, fluorine, chlorine, cyano, methyl, ethyl, n-propyl, isopropyl, methoxy, ethoxy, methoxymethyl or cyclopropyl,
R⁴ represents a group of the formula where
* is the point of attachment to the carbonyl group,
R⁷ represents fluorine, chlorine or methyl,
and
R⁹ represents hydrogen.

4. A compound according to claim 1, wherein
E represents a group of the formula

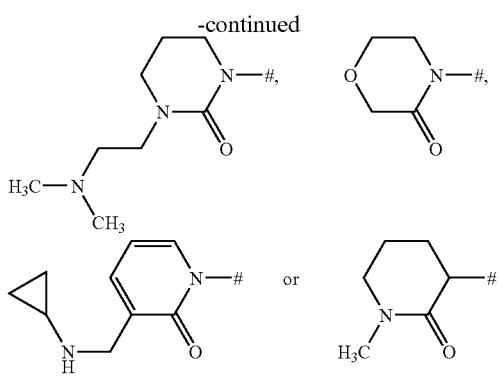

where
# is the point of attachment to the phenyl ring,

A represents pyrazolyl, oxadiazolyl or isoxazolinyl,
where pyrazolyl, oxadiazolyl and isoxazolinyl are attached in the 1-position to the phenyl ring and pyrazolyl, oxadiazolyl and isoxazolinyl for their part have a 1,3-attachment to the phenyl ring and the carbonylaminomethyl group,
and
where pyrazolyl, oxadiazolyl and isoxazolinyl are substituted by a substituent $R^6$,
where $R^6$ is attached to the neighbouring atom of the atom to which the carbonylaminomethyl group is attached and has a 1,4-attachment to the phenyl ring
and
where the atom to which $R^6$ is attached is a nitrogen or carbon atom
and
where
$R^6$ represents phenyl, pyrid-2-yl, pyrid-3-yl or pyrid-4-yl, where phenyl, pyrid-2-yl, pyrid-3-yl and pyrid-4-yl may be substituted by a substituent, where the substituent is selected from the group consisting of halogen, hydroxy, amino, $C_1$-$C_4$-alkyl, $C_1$-$C_4$-alkoxy, $C_1$-$C_4$-alkylamino, hydroxycarbonyl, aminocarbonyl, $C_1$-$C_4$-alkoxycarbonyl and $C_1$-$C_4$-alkylaminocarbonyl, $R^2$ represents hydrogen or fluorine,
$R^3$ represents hydrogen, fluorine, chlorine, methyl or methoxy,
$R^4$ represents a group of the formula

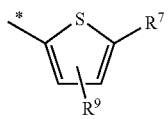

where
* is the point of attachment to the carbonyl group, $R^7$ represents chlorine,
and
$R^9$ represents hydrogen.

5. A method for preparing a compound of the formula (I) or one of its salts, its solvates or the solvates of its salts according to claim 1, comprising reacting a compound of the formula

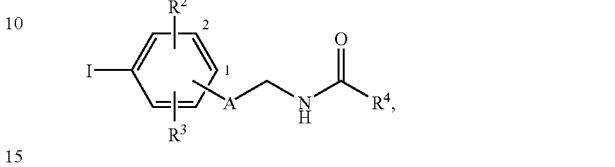

(II)

in which A, $R^2$, $R^3$ and $R^4$ have the meaning given in claim 1, with a compound of the formula

E—H   (III), in which E has the meaning given in claim 1.

6. A compound according to claim 1 for preventing blood coagulation in vitro.

7. A pharmaceutical composition, comprising a compound according to claim 1 in combination with an inert non-toxic pharmaceutically acceptable auxiliary.

8. The pharmaceutical composition of claim 7 further comprising a second active compound selected from the group consisting of a lipid-lowering agent, a cornary therapeutics/vasodilator, a plasminogen activator, an anticoagulant, a platelet aggregation inhibiting substance, a fibrinogen receptor antagonist, and an antiarrhythmic.

9. A pharmaceutical composition of claim 7 for the treatment and/or prophylaxis of thromboembolic disorders.

10. A method for the treatment and/or prophylaxis of thromboembolic disorders in humans and animals comprising administering an anticoagulatory effective amount of at least one compound according to claim 1.

11. A method for preventing blood coagulation in a biological sample in vitro, wherein an anticoagulatory effective amount of a compound according to claim 1 is added to the biological sample.

12. A method for the treatment and/or prophylaxis of a thromboembolic disorder in a human or animal comprising administering an antiocoagulatory effective amount of a pharmaceutical composition of claim 7 thereto.

13. The method of claim 11, wherein the biological sample is banked blood or a biological sample comprising factor Xa.

14. The method of claim 12, wherein the thromboembolic disorder is selected from the group consisting of ST-elevation myocardial infarction, non-ST-elevation myocardial infarction, stable angina pectoris, unstable angina pectoris, reocclusions and restenoses after coronary interventions, peripheral arterial occlusive diseases, pulmonary embolisms, deep vein thromboses and kidney vein thromboses, transitory ischaemic attacks, and thrombotic and thromboembolic stroke.

* * * * *